United States Patent [19]

Klaus et al.

[11] Patent Number: 5,300,522
[45] Date of Patent: Apr. 5, 1994

[54] CONDENSED HETEROCYCLIC COMPOUNDS AND PHARMACEUTICAL USE THEREOF

[75] Inventors: Michael Klaus, Weil/Rhein, Fed. Rep. of Germany; Peter Mohr, Basel, Switzerland; Ekkehard Weiss, Inzlingen, Fed. Rep. of Germany

[73] Assignee: Hoffmann-La Roche Inc., Nutley, N.J.

[21] Appl. No.: 931,612

[22] Filed: Aug. 18, 1992

Related U.S. Application Data

[62] Division of Ser. No. 696,812, May 28, 1991, Pat. No. 5,164,387, which is a division of Ser. No. 377,510, Jul. 10, 1989, Pat. No. 5,037,825.

[30] Foreign Application Priority Data

Jul. 14, 1988 [CH] Switzerland .................. 2694/88
May 26, 1989 [CH] Switzerland .................. 1994/89

[51] Int. Cl.$^5$ ............... A61K 31/34; A61K 31/35; C07D 307/80; C07D 311/58
[52] U.S. Cl. .................. 514/450; 514/228.2; 514/233.5; 514/255; 514/456; 514/469; 544/58.7; 544/62; 544/147; 544/151; 544/153; 544/376; 549/355; 549/398; 549/404; 549/405; 549/408; 549/409; 549/462
[58] Field of Search ............ 549/355, 404, 405, 407, 549/468, 462, 408, 409, 398; 514/450, 456, 469

[56] References Cited

U.S. PATENT DOCUMENTS

| 3,635,941 | 1/1972 | Weaver et al. | 534/770 |
| 4,678,793 | 7/1987 | Klaus et al. | 549/23 |
| 4,808,597 | 2/1989 | Hoffman et al. | 514/432 |
| 4,826,984 | 5/1984 | Berlin et al. | 549/23 |

FOREIGN PATENT DOCUMENTS

86259 1/1986 Luxembourg.
85-00806 2/1985 World Int. Prop. O. .

OTHER PUBLICATIONS

Mentzer et al, Chemical Abstracts, vol. 66 (1967) 18193n.

(List continued on next page.)

*Primary Examiner*—Richard L. Raymond
*Attorney, Agent, or Firm*—George M. Gould; William H. Epstein; Bruce A. Pokras

[57] ABSTRACT

The invention relates to compounds of the formula

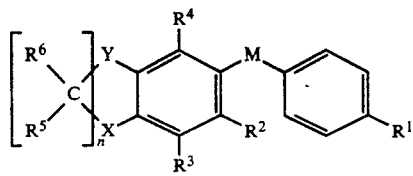

wherein $R^1$ is hydrogen, acyl, lower-alkyl or —CHO, —CH$_2$OR$^{10}$, —COR$^7$ or OR$^{13}$; $R^2$, $R^3$ and $R^4$ are, independently, hydrogen, lower-alkyl, lower-alkoxy or halogen; $R^5$ and $R^5$ are, independently, hydrogen or lower-alkyl; $R^7$ is hydroxy, lower-alkoxy or NR$^8$R$^9$; $R^8$ and $R^9$ are, independently, hydrogen or lower-alkyl; X and Y are, independently, >CR$^{14}$R$^{15}$, —O—, —S—, >SO, >SO$_2$ or >NR$^{18}$; R$^{10}$ and R$^{18}$ are, independently, hydrogen, lower-alkyl or acyl; M is —C(R$^{11}$)=C(R$^{12}$)—, —CONH— or —NH—CO—; R$^{11}$, R$^{12}$, R$^{14}$ and R$^{15}$ are, independently, hydrogen or lower-alkyl, R$^{13}$ is hydrogen, lower-alkoxycarbonyl or lower- alkyl, which can be substituted by amino, mono-alkylamino, di-alkylamino, morpholino, thiomorpholino or piperazino; and n is 1, 2, 3 or 4; with the proviso that at least one of X and Y comprises a hetero atom and that n is 1, 3 or 4 when X contains a hetero atom, Y is >C(CH$_3$)$_2$ and R$^1$ is lower-alkyl or —CH$_2$OR$^{10}$ or —COR$^7$, or a salt of a compound of formula I, when R$^1$ is carboxy.

The compounds of formula I are useful in the treatment and prophylaxis of neoplasms, dermatoses and ageing of the skin.

20 Claims, No Drawings

OTHER PUBLICATIONS

Ohsumi et al, *Chemical Abstracts*, vol. 112 (1990) 50495s.

R. S. Tewari et al., *Chemical Abstracts*, 84:73777c, p. 406 (1976).

R. Sahdev et al., *Chemical Abstracts*, 84:150546f, p. 541 (1976).

D. T. Witiak et al., *Journal of Organic Chemistry*, 38 (9), pp. 1242–1247 (1974).

H. Hirose, *Chemical Abstracts*, 105: 235743v, p. 595 (1986).

K. Berlin et al., *Chemical Abstracts*, 111:173986q, p. 713 (1989).

Y. P. Talwar et al., *Chemical Abstracts*, 70 77526d, p. 299 (1969).

G. Savona et al., *J. Heterocyclic Chem.*, 8, pp. 681–684 (1971).

M. Botta et al., *Tetrahedron Letters*, 29 (22), pp. 2741–2744 (1988).

V. S. Fedorov et al *Chemical Abstracts*, 83: 97106b, p. 574 (1975).

CONDENSED HETEROCYCLIC COMPOUNDS AND PHARMACEUTICAL USE THEREOF

This is a division of application Ser. No. 07/696,812 filed May 28, 1991, now U.S. Pat. No. 5,164,387, which was a division of application Ser. No. 07/377,510 filed Jul. 10, 1989, now U.S. Pat. No. 5,037,825.

BRIEF SUMMARY OF THE INVENTION

The invention relates to condensed heterocyclic compounds of the formula

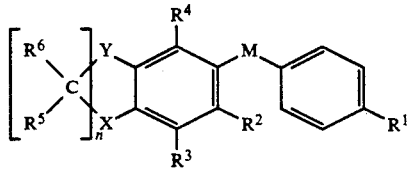

I wherein $R^1$ is hydrogen, acyl, lower-alkyl or a group —CHO, —CH$_2$OR$^{10}$, —COR$^7$ or OR$^{13}$; $R^2$, $R^3$ and $R^4$ are, independently, hydrogen, lower-alkyl, lower-alkoxy or halogen; $R^5$ and $R^6$ are, independently, hydrogen or lower-alkyl; $R^7$ is hydroxy, lower-alkoxy or NR$^8$R$^9$; $R^8$ and $R^9$ are, independently, hydrogen or lower-alkyl; X and Y are, independently, >CR$^{14}$R$^{15}$, —O—, —S—, >SO, >SO$_2$ or >NR$^{18}$; $R^{10}$ and $R^{18}$ are, independently, hydrogen, lower-alkyl or acyl; M is —C(R$^{11}$)=C(R$^{12}$)—, —CONH— or —NH—CO—; $R^{11}$, $R^{12}$, $R^{14}$ and $R^{15}$ are, independently, hydrogen or lower-alkyl, $R^{13}$ is hydrogen, lower-alkoxycarbonyl or lower-alkyl, which can be substituted by amino, monoalkylamino, di-alkylamino, morpholino, thiomorpholino or piperazino; and n is 1, 2, 3 or 4; with the proviso that at least one of X and Y comprises a hetero atom and that n is 1, 3 or 4 when X contains a hetero atom, Y is >C(CH$_3$)$_2$ and $R^1$ is lower-alkyl or —CH$_2$OR$^{10}$ or —COR$^7$, and salts of the compounds of formula I, when $R^1$ is a carboxy group.

In another aspect, the invention relates to a process for the preparation of the compounds of formula I, pharmaceutical preparations based on the compounds of formula I, the compounds of formula I in the treatment and prophylaxis of neoplasms, dermatoses and aging of the skin as well as the use of the compounds of formula I in the preparation of pharmaceutical preparations for the treatment and prophylaxis of such disorders.

DETAILED DESCRIPTION OF THE INVENTION

The invention relates to condensed heterocyclic compounds of the formula

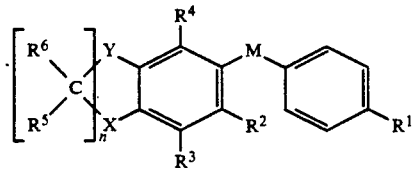

I wherein $R^1$ is hydrogen, acyl, lower-alkyl or a group —CHO, —CH$_2$OR$^{10}$, —COR$^7$ or OR$^{13}$; $R^2$, $R^3$ and $R^4$ are, independently, hydrogen, lower-alkyl, lower-alkoxy or halogen; $R^5$ and $R^6$ are, independently, hydrogen or lower-alkyl; $R^7$ is hydroxy, lower-alkoxy or NR$^8$R$^9$; $R^8$ and $R^9$ are, independently, hydrogen or lower-alkyl; X and Y are, independently, >CR$^{14}$R$^{15}$, —O—, —S—, >SO, >SO$_2$ or >NR$^{18}$; $R^{10}$ and $R^{18}$ are, independently, hydrogen, lower-alkyl or acyl; M is —C(R$^{11}$)=C(R$^{12}$)—, —CONH— or —NH—CO—; $R^{11}$, $R^{12}$, $R^{14}$ and $R^{15}$ are, independently, hydrogen or lower-alkyl, $R^{13}$ is hydrogen, lower-alkoxycarbonyl or lower-alkyl, which can be substituted by amino, monoalkylamino, di-alkylamino, morpholino, thiomorpholino or piperazino; and n is 1, 2, 3 or 4; with the proviso that at least one of X and Y comprises a hetero atom and that n is 1, 3 or 4 when X contains a hetero atom, Y is >C(CH$_3$)$_2$ and $R^1$ is lower-alkyl or —CH$_2$OR$^{10}$ or —COR$^7$, and salts of the compounds of formula I, when $R^1$ is a carboxy group.

Furthermore, the invention relates to a process for the preparation of the compounds of formula I, pharmaceutical preparations based on the compounds of formula I, the compounds of formula I in the treatment and prophylaxis of neoplasms, dermatoses and aging of the skin as well as the use of the compounds of formula I in the preparation of pharmaceutical preparations for the treatment and prophylaxis of such disorders.

The term "lower" denotes groups with 1–6 C atoms. The terms "alkyl", and "alkoxyl" groups denote straight-chain or branched hydrocarbons, such as methyl, ethyl, propyl, isopropyl, butyl, sec.-butyl or tert.-butyl and methoxy, ethoxy, propoxy, isopropoxy, butoxy, sec.-butoxy and tert.-butoxy, respectively. Examples of acyl groups are alkanoyl groups, preferably lower-alkanoyl groups such as acetyl, propionyl, butyryl, pivaloyl and caproyl; or aroyl groups such as benzoyl, p-nitrobenzoyl and toluoyl; or aralkanoyl groups, for example, phenylalkanoyl, such as phenylacetyl.

A preferred group of compounds of formula I comprises those in which Y is —O—, —S—, >SO, >SO$_2$ or >NR$^{18}$. Furthermore, compounds of formula I in which X and Y are —O—, —S—, >SO, >SO$_2$ or >NR$^{18}$, especially those in which X and Y are —S—, are preferred. Preferably, n is 2 or 3, especially 3. M preferably is —C(R$^{11}$)=C(R$^{12}$), especially —C(CH$_3$)=CH—; and —CONH—.

The compounds of formula I can be prepared in accordance with the invention by a) reacting a compound of the formula

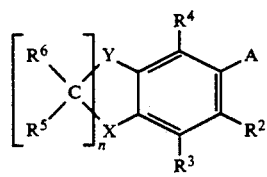

II with a compound of the formula

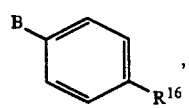

III wherein either A is the residue —CH(R$^{11}$)P$^+$(Q)$_3$Z$^-$ or —CH(R$^{11}$)—P(O)(OAlk)$_2$ and B is R$^{12}$—CO—; or A is R$^{11}$—CO— and B is the residue —CH(R$^{12}$)P$^+$(Q)$_3$Z$^-$ or —CH(R$^{12}$)—P—(O)(OAlk)$_2$; Q is aryl; Z$^-$ is an anion of an organic or inorganic acid; Alk is lower alkyl; and R[16] is R[1] with the exception of the formyl, carboxyl, hydroxy and hydroxymethyl group; or b) reacting a compound of the formula

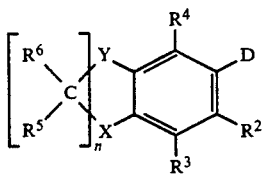
IV with a compound of the formula

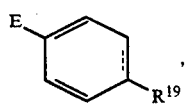
V wherein either D is a carboxyl group or a reactive derivative thereof and E is an amino group or D is an amino group and E is a carboxyl group or a reactive derivative thereof and R[19] is a residue R[1] with the exception of the carboxyl, hydroxymethyl and hydroxy group;

c) reacting a compound of the formula

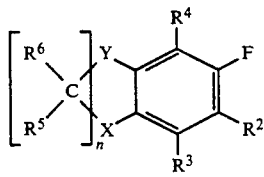
VI with a compound of the formula

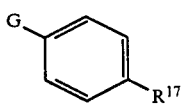
VII wherein either F is —CH(R[11])MgHal and G is R[12]—C(O)—; or F is R[12]—C(O)— and G is —CHC(R[12])MgHal; Hal is halogen and R[17] is hydrogen, lower-alkyl or —OR[13]; and whereby the remaining symbols are as described earlier in formulas II–VII; and dehydrating the reaction product;

whereupon, if desired, in the resulting reaction product of formula I, the residue R[1] is functionally modified and/or the sulfur atom is a compound I wherein X and/or Y is —S— is oxidized to a sulfoxyl or sulfonyl group.

The reaction of the compounds II and III, in accordance with process variant a), can be carried out according to the known Wittig or Horner reaction.

In the case of the Wittig reaction, that is, using a compound of formula II wherein A=—CH(R[11])P+(Q)₃Z− or of formula III wherein B=—CH(R[12])P+(Q)₃Z−, the components are reacted with one another in the presence of an acid-binding agent, for example, in the presence of a strong base such as for example, butyllithium, sodium hydride or the sodium salt of dimethyl sulfoxide, or potassium tertbutylate, but especially in the presence of an ethylene oxide which is optionally substituted by lower-alkyl such as 1,2-butylene is oxide, optionally in a solvent, for example, in an ether such as diethyl ether or tetrahydrofuran or in an aromatic hydrocarbon such as benzene, at a temperature in the range of between room temperature and the boiling point of the reaction mixture.

Of the inorganic acid anions Z−, the chloride or bromide ion or the hydrosulfate ion is preferred and of the organic acid anions the tosyloxy ion is preferred. The aryl residue Q is preferably phenyl.

In the case of the Horner reaction, that is, using a compound of formula II wherein A=—CH(R[11])P(O)(OAlk)₂ or of formula III wherein B=—CH(R[12])P(O)(OAlk)₂, the components are condensed with the aid of a base and preferably in the presence of an inert organic solvent, for example, with the aid of sodium hydride in benzene, toluene, dimethylformamide, tetrahydrofuran, dioxane or 1,2-dimethoxyethane, or also with the aid of a sodium alcoholate in an alkanol, for example, sodium methylate in methanol, at a temperature range of between 0° and the boiling point of the reaction mixture. The alkoxy residues in A and B are preferably lower alkoxy residues of 1–6 carbon atoms such as methoxy or ethoxy.

Compounds of formula I wherein M is —C(R[11])=C(R[12])— are obtained in accordance with process variant a).

The reaction of a compound IV with a compound V in accordance with process variant b), can be carried out according to known methods for the acylation of amines. Preferably, a compound of formula IV wherein D is a carboxylic acid halide group, for example, the group —COCl, is reacted with a compound of formula V wherein E is —NH₂ to give a compound of formula I wherein M is —CONH— or an amine of formula IV is reacted with a carboxylic acid halide of formula V to give a compound of formula I wherein M is —NH—CO—. The acylations are conveniently carried out in the presence of a base, for example, an organic base such as pyridine.

The reaction of the compounds of formulas VI and VII in accordance with process variant c), can be carried out in a known manner under the conditions of a Grignard reaction, for example, in an ether such as diethyl ether or tetrahydrofuran at room temperature and subsequent water-cleavage with an acidic agent, for example, with an organic acid such as p-toluenesulfonic acid. According to this process variant, there are obtained compounds of formula I wherein M is —C(R[11])=C(R[12])— and R[1] is R[17] as described above.

As functional modifications of a substituent R[1] in a resulting compound of formula I, there come into consideration, for example, the saponification of a carboxylic acid ester or its reduction to the hydroxymethyl group. The hydroxymethyl group can also be oxidized to the formyl group or can be esterified or etherified. Furthermore, a carboxyl group can be converted into a salt, an ester, an amide or the hydroxymethyl group.

All of these modifications can be carried out according to known methods.

A carboxylic acid ester of formula I can be amidated directly, as described hereinafter, or can be hydrolyzed in a known manner, for example, by treatment with alkalis, especially by treatment with aqueous-alcoholic sodium hydroxide solution or potassium hydroxide solution at a temperature in the range of between room temperature and the boiling point of the reaction mixture, to the carboxylic acid which can be amidated via an acid halide.

A carboxylic acid of formula I can be converted in a known manner, for example, by treatment with thionyl chloride or phosphorus trichloride in toluene or oxalyl chloride in dimeihylformamide/benzene, into the acid chloride which can be converted by reaction with alcohols into esters or with amines into the corresponding amide.

A carboxylic acid ester of formula I can be converted, for example, by treatment with lithium amide directly into the corresponding amide. The lithium amide is advantageously reacted with the respective ester at room temperature.

A carboxylic acid or a carboxylic acid ester of formula I can be reduced in a known manner to the corresponding alcohol of formula I. The reduction is advantageously carried out with the aid of a metal hydride or alkyl metal hydride in an inert solvent. Mixed metal hydrides such as lithium aluminum hydride or bis-[methoxy-ethoxy]-sodium aluminum dihydride have been found to be particularly suitable hydrides. As solvents there can be used, inter alia, ethers, tetrahydrofuran or dioxane when lithium aluminum hydride is used; and ethers, hexane, benzene or toluene when diisobutylaluminum hydride or bis-[methoxy-ethoxy]-sodium aluminum dihydride is used.

An alcohol of formula I can be etherified, for example, in the presence of a base, preferably in the presence of sodium hydride, in an organic solvent such as dioxan, tetrahydrofuran, 1,2-dimethoxyethane, dimethylformamide, at a temperature in the range of between 0° and room temperature with an alkyl halide, for example, with methyl iodide.

An alcohol of formula I can also be esterified by treatment with an alkanoyl halide or anhydride, conveniently in the presence of a base, for example, in the presence of pyridine or triethylamine, at a temperature in the range of between room temperature and the boiling point of the reaction mixture.

The carboxylic acids of formula I form salts with bases, especially with the alkali metal hydroxides, preferably with sodium hydroxide or potassium hydroxide.

A compound of formula I wherein X and/or Y is —S— can be oxidized using known methods to give a compound of formula I wherein X and/or Y is =SO or =SO$_2$. The oxidation to-the sulfoxide group can be carried out with oxidizing agents such as periodates, for example, NaIO$_4$ or with organic peroxides such as m-chloroperbenzoic acid. The oxidation with organic peracids is carried out using about one equivalent of peracid in order to obtain a sulfoxide compound (X/Y=SO), whereas the use of two equivalents of peracid leads to sulfones (X/Y=SO$_2$).

The compounds of formula I wherein M contains a C—C double bond can be present in the trans or cis form. When prepared, they occur predominantly in the trans form. Where desired, cis components which may be obtained can be separated or isomerized in a known manner.

The compounds of formulas II–V, which are used as starting materials for the preparation of the compounds of formula I, insofar as they are not knower or are not described hereinafter, can be prepared in analogy to known methods or to the methods described hereinafter.

The compounds of formula I and their physiologically compatible salts are pharmacodynamically valuable compounds. They can be used for the topical and systemic therapy of benign and malignant neoplasms, of premalignant lesions as well as, further, for the systemic and topical prophylaxis of the said conditions.

Furthermore, they are suitable for the topical and systemic therapy of acne, psoriasis and other dermatoses which are accompanied by an intensified or pathologically altered cornification, as well as of inflammatory and allergic dermatological conditions and of light-damaged (aged) skin. Further, they can also be used for the control of mucous membrane disorders with inflammatory or degenerative or metaplastic changes. In the papilloma test, (Europ. J. Cancer Vol. 10, pp. 731–737, 1974) ethyl p-[2--(3,4-dihydro-4,4-dimethyl-2H-1-benzopyran-7-yl) propenyl]benzoate (Example 1) and p-[2-(1,2,3,4-tetrahydro-1,1,4-trimethyl-7-quinolinyl)propenyl]benzoic acid (Example 5) in a dosage of 6 mg/kg/week showed a papilloma regression of 66 and 42%, respectively; p[2-(3,4-dihydro-4,4-dimethyl-2H-1-thiobenzopyran-7-yl) propenyl]benzoic acid (Example 3) in a dosage of 3 mg/kg/week showed a papilloma regression of 61% and ethyl p[(E)-2-(3,4-dihydro-3,3-dimethyl-2H-1,5-benzodithiepin-7-yl)propenyl]benzoate in a dosage of 50 mg/kg/week showed a papilloma regression of 50%.

The compounds of formula I can also be used for the treatment of inflammatory, allergic, rheumatic and immunological disorders in a wide variety-of organs. Examples of such disorders are: primary-chronic polyarthritis, spondylarthritis ancylopoetica, osteoarthritides, arthritides and arthroses; eczemas, a topical dermatitis, allergic rhinitis, bronchial asthma; autoimmune disorders, for example, Lupus erythematosus and Reiter's syndrome.

The compounds of formula I and their aforementioned salts can accordingly be used as medicaments, for example, in the form of pharmaceutical preparations.

The compositions can be administered enterally, parenterally or topically. For enteral administration suitable for example, compositions in the form of tablets, capsules, dragees, syrups, suspensions, solutions and suppositories. Preparations in the form of infusions or injections are suitable for parenteral administration.

The dosages at which in the preparations are administered can vary according to the mode of administration and route of administration as well as according to the requirements of the host requiring such treatment.

In the case of oral administration of the compounds in accordance with the invention, dosages of about 0.1–100 mg/kg per day, preferably 0.5–50 mg/kg, come into consideration for adults.

The preparations can be administered in one or several doses. Capsules containing about 5–500 mg of active ingredient are a preferred administration form.

The preparations can contain inert or pharmacodynamically active additives. Tablets or granulates, for example, can contain a series of binding agents, filler materials, carrier substances or diluents. Liquid preparations can be present, for example, in the form of sterile solution which is miscible with water. Capsules can contain a filler material or thickening agent in addition to the active ingredient. Furthermore, flavor-improving additives as well as the substances usually used as preserving, stabilizing, moisture-retaining and emulsifying agents, salts for varying the osmotic pressure, buffers and other additives,can also be present.

The previously mentioned carrier substances and diluents can be organic or inorganic substances, for example, of water, gelatin, lactose, starch, magnesium stearate, talc, gum arabic, polyalkylene glycols and the like. It is a prerequisite that all adjuvants used in the preparation of the preparations are non-toxic.

For topical use, the active ingredients are conveniently used in the form of salves, tinctures, creams, solutions, lotions, sprays, suspensions and the like. Salves and creams as well as solutions are preferred. These preparations intended for topical use can be prepared by mixing the aforementioned compounds and salts as active ingredients with non-toxic, inert, solid or liquid carriers which are usual in such preparations and which are suitable for topical treatment.

For topical use, conveniently suitable preparations comprise about 0.1–5%, preferably 0.3–2%, solutions as well as about 0.1–5%, preferably about 0.3–2%, salves or creams.

If desired, an antioxidant, for example, tocopherol, N-methyl-γ-tocopheramine as well as t-butyl-hydroxyanisole or t-butyl-hydroxytoluene, can be admixed with the preparations.

EXAMPLE 1

0.5 g of a 50% suspension of sodium hydride in mineral oil were suspended in 15 ml of dimethyl sulfoxide and treated under argon with a solution of 3.2 g of diethyl (4-carbethoxybenzyl)phosphonate in 10 ml of dimethyl sulfoxide. The mixture was subsequently heated to 40° C. for 20 minutes, cooled to room temperature, a solution of 0.87 g of 3,4-dihydro-4,4-dimethyl-7-acetyl-2H-1-benzopyran in 5 ml of dimethyl sulfoxide was added dropwise thereto and the mixture was heated to 40° C. for 1 hour. The reaction mixture obtained was poured on to ice/water, acidified with 1N hydrochloric acid and extracted repeatedly with ether. The organic phase was washed with water, dried and evaporated. There was obtained a yellowish oil which, after filtration over a short column (silica gel, eluting agent hexane/ethyl acetate=9:1), crystallized from hexane and yielded 0.9 g of ethyl p-[2-(3,4-dihydro-4,4-dimethyl-2H-1-benzopyran-7-yl)propenyl]benzoate, m.p. 48°–50° C.

The 3,4-dihydro-4,4-dimethyl-7-acetyl-2H-1-benzopyran used as the starting material can be prepared as follows:

A mixture of 20 g of 3-bromophenol, 92 g of ethyl acrylate and 1.8 ml of Triton B (35% in methanol) was boiled at reflux overnight. After distilling off the excess acrylate at normal pressure, the residue was distilled in a high vacuum. There were obtained 16.7 g of ethyl 3-(m-bromophenoxy)propionate as a colorless oil, boiling point 107°–110° C./67 Pa.

4.4 g of Magnesium shavings were covered with 40 ml of ether and treated over a period of 30 minutes with a solution of 32 g of methyl iodide in 70 ml of ether. After boiling under reflux for an additional 30 minutes, a solution of 16.7 g of ethyl 3-(m-bromophenoxy)propionate in 70 ml of benzene was added dropwise thereto while cooling. The reaction mixture was heated to reflux for 1.5 hours and subsequently treated with 210 ml of saturated ammonium chloride solution while cooling with ice. After repeated extraction of the reaction mixture with ether, washing of the organic with water, drying and evaporation there was obtained an oil which was purified further by filtration over a short column (SiO2, eluting agent hexane/ethyl acetate=9:1). There were obtained 14 g of 4-(m-bromo- phenoxy)-2-methyl-2-butanol as a colorless oil, boiling point 106° C./40 Pa.

9.8 g of Aluminum chloride were dissolved in 100 ml of nitromethane and treated in the course of 40 minutes at room temperature with a solution of 14 g of 4-(m-bromophenoxy)-2-methyl-2-butanol in 100 ml of nitromethane. The mixture was stirred at room temperature for an additional 1.5 hours, cooled to 0° C. and 200 ml of 2N hydrochloric acid and 300 ml of water were added dropwise thereto in succession.

After extraction of the reaction mixture with ether, drying and evaporation of the organic phase, the thus-obtained red-brown oil was first filtered over a column (SiO2, eluting agent hexane/ethyl acetate=9:1) and subsequently distilled in a high vacuum. There were obtained 8 g of 7-bromo-3,4-dihydro-4,4-dimethyl-2H-1-benzopyran as a colorless oil, boiling point 82°–86° C./0.5 mm. This substance still contained some 5-bromo-3,4-dihydro-4,4-dimethyl-2H-1-benzopyran and was used in this form in the next step.

1 g of Magnesium shavings was covered with 10 ml of absolute tetrahydrofuran and treated dropwise at 50°–60° C. using an ultrasonics bath with a solution of 10 g of 7-bromo-3,4-dihydro-4,4-dimethyl-2H-1-benzopyran in 50 ml of tetrahydrofuran. Thereafter, the mixture was heated to 70° C. for an additional 2 hours, cooled to 0° C. and a solution of 9.5 g of acetaldehyde in 30 ml of tetrahydrofuran was added dropwise thereto. The mixture was stirred at room temperature for an additional hour, poured on to ice/saturated ammonium chloride solution, extracted with ether, washed with water, dried and evaporated. After chromatography (silica gel, eluting agent hexane/ethyl acetate 4:1) there were obtained 6.9 g of 3,4-dihydro-α,4,4-trimethyl-7-(2H-1-benzopyran)methanol as a viscous oil.

5.9 g of 3,4-dihydro-α,4,4-trimethyl-7-(2H-1-benzopyran)-methanol were dissolved in 200 ml of methylene chloride and treated with 25 g of manganese dioxide. After stirring at room temperature for 3 hours, the reaction mixture was filtered and the filtrate was evaporated. There were obtained 5.8 g of 3,4-dihydro-4,4-dimethyl-7-acetyl-2H-1-benzopyran as a colorless oil.

EXAMPLE 2

0.5 g of the ethyl ester from Example 1 was dissolved in 20 ml of ethanol and treated with a solution of 0.8 g of potassium hydroxide in 5 ml of water. After stirring at 50° C. for 2 hours, the mixture was poured on to ice/water, acidified with 2N hydrochloric acid and extracted repeatedly with ethyl acetate. After washing the organic phase with water, drying over sodium sulfate, evaporation and crystallization from ethyl acetate, there were obtained 350 mg of p-[2-(3,4-dihydro-4,4-dimethyl-2H-1-benzopyran-7-yl)propenyl]benzoic acid, m.p. 242°–244° C.

EXAMPLE 3

18.9 g of [1(3,4-dihydro-4,4-dimethyl-2H-1-benzothiopyran-7-yl)ethyl]]triphenylphosphonium bromide were suspended in 200 ml of 1,2-butylene oxide and heated at reflux for 16 hours with 5.7 g of ethyl 4-formyl-benzoate. After cooling, the clear reaction mixture was poured into a mixture of methanol and water (6:4), extracted three times with hexane, washed with methanol/water (6:4) and water, dried and evaporated. The yellow oil obtained was filtered over silica gel (eluting agent hexane/ethyl acetate 19:1) and crystallized from hexane/ethyl acetate. There were obtained 5.9 g of ethyl p-[2-(3,4-dihydro-4,4-dimethyl-2H-1-benzothiopyran-7-yl)propenyl]benzoate in the form of colorless crystals, m.p. 64°–65° C.

1 g of the thus-obtained ester was dissolved in 20 ml of ethanol and treated with a solution of 1.6 g of potassium hydroxide in 10 ml of water. After heating to 50° C. for 2 hours, the mixture was poured on to ice, acidified with 2N hydrochloric acid and extracted repeatedly with ethyl acetate. The crystalline residue obtained after evaporation was recrystallized from acetic acid. There was obtained 0.6 g of p-[2-(3,4-dihydro-4,4-dimethyl-2H-1-benzothiopyran-7-yl)propenyl]benzoic acid, m.p. 255°-257° C.

The phosphonium salt used as the starting material can be prepared as follows:

36 g of 3-bromothiophenol were dissolved in 400 ml of dimethylformamide. After the addition of 27 g of finely powdered potassium carbonate and 29 g of 3,3-dimethylallyl bromide, the mixture was stirred at room temperature for 1 hour, diluted with 500 ml of water, acidified with 3N hydrochloric acid while cooling and extracted with ether. The yellow-brown oil obtained after evaporation was distilled in a high vacuum. There were obtained 48 g of m-bromophenyl 3-methyl-2-butenyl sulfide as a colorless liquid, boiling point 85° C./13.3 Pa.

46.5 g of this sulfide were dissolved in 800 ml of toluene and, after the addition of 45 g of p-toluenesulfonic acid monohydrate, boiled for 10 hours on a water separator. The cooled reaction mixture was diluted with water, neutralized by the addition of aqueous sodium bicarbonate solution and extracted with ethyl acetate. The yellow-brown oil obtained after evaporation of the solvent was distilled in a high vacuum. There were obtained 39 g of 7-bromo-3,4-dihydro-4,4-dimethyl-2H-1-benzothiopyran as a slightly yellowish oil, boiling point 90°-93° C./13.3 Pa. The compound contained about 15% of 5-bromo-3,4-dihydro-4,4-dimethyl-2H-1-benzothiopyran and was used in this form in the next step.

1.85 g of Magnesium shavings were covered with 20 ml of absolute tetrahydrofuran. While heating to reflux, there was added dropwise thereto a solution of 10.8 g of the mixture obtained in the previous step in 80 ml of tetrahydrofuran and the mixture was boiled until practically all of the magnesium had dissolved. After cooling to 0° C., a solution of 8.5 g of acetaldehyde in 50 ml of tetrahydrofuran was added dropwise thereto and the mixture was stirred at room temperature for an additional 30 minutes. The reaction mixture was poured into ice-cold ammonium chloride solution, extracted with ethyl acetate, washed with water and evaporated. After filtration over silica gel (eluting agent hexane/ethyl acetate=19:1), there were obtained 13.5 g of 3,4-dihydro-α,4,4-trimethyl-7-(2H-1-benzothiopyran)methanol as a slightly yellow, viscous oil.

This oil was dissolved in 250 ml of acetonitrile and treated with 23 g of triphenylpnosphine hydrobromide. After heating to 60° C. for 20 hours, the reaction mixture was evaporated. The residue was taken up with 500 ml of 80% aqueous ethanol and extracted three times with hexane. The ethanol solution was evaporated. The residue was dissolved in methylene chloride, dried over sodium sulfate and evaporated. There was obtained a foamy residue which was converted by trituration with ether into an amorphous, filterable substance, whereby 26 g of [1-(3,4-dihydro-4,4-dimethyl-2H-1-benzothiopyran-7-yl)-ethyl]triphenylphosphonium bromide were obtained.

EXAMPLE 4

2.5 g of ethyl p-[2-(3,4-dihydro-4,4-dimethyl-2H-1-benzothiopyran-7-yl)propenyl]benzoate were dissolved in 30 ml of chloroform and treated dropwise at 0° C. with a solution of 2.7 g of 90% m-chloroperbenzoic acid in 40 ml of chloroform. Depending on the content of the peracid some more m-chloroperbenzoic acid must be added until the sulfoxide resulting as an intermediate has disappeared completely. The reaction mixture was diluted with chloroform, extracted twice with ice-cold dilute, aqueous sodium carbonate solution, washed twice with water, dried and evaporated. After chromatography of the crude product (silica gel, eluting agent hexane/ethyl acetate=4:1) and crystallization from ethyl acetate/hexane, there were obtained 1.4 g of ethyl p-[2-(3',4'-dihydro-4',4'-dimethyl-2'H-1-benzothiopyran-7'-yl)propenyl]benzoate 1',1'-dioxide in the form of colorless crystals, m.p. 90°-91° C.

Hydrolysis of the thus-obtained ethyl ester with potassium hydroxide in aqueous-ethanolic solution in analogy to Example 3 gave, after recrystallization from tetrahydrofuran/ethyl acetate/hexane, p-[2-(3',4'-dihydro-4',4'-dimethyl-2'H-1-benzothiopyran-7'-yl)propenyl]benzoic acid 1',1'-dioxide in the form of colorless crystals, m.p. 163°-265° C.

EXAMPLE 5

2.9 g of a 50% suspension of sodium hydride in mineral oil were suspended in 30 ml of dimethylformamide after two-fold washing with pentane and treated dropwise at room temperature with a solution of 17.3 g of diethyl (4-carbethoxybenzyl)phosphonate in 50 ml of dimethylformamide. After stirring at room temperature for 1 hour, a solution of 5 g of 1,2,3,4-tetrahydro-1,4,4-trimethyl-7-quinolinyl methyl ketone in 50 ml of dimethylformamide was added dropwise thereto. The reaction mixture was heated to 50° C. for 1 hour, poured on to ice/water and extracted with ethyl acetate. The brownish oil obtained after drying and evaporation of the organic phase was chromatographed (silica gel, eluting agent hexane/ethyl acetate=9:1) and gave 4.2 g of ethyl p-[2-(1,2,3,4-tetrahydro-1,4,4-trimethyl-7-quinolinyl)propenyl]benzoate as a slightly yellow, viscous oil.

3.2 g of this oil were dissolved in 30 ml of ethanol and treated with a solution of 5 g of potassium hydroxide in 20 ml of water. After heating to 50° C. for 2 hours, the mixture was poured on to ice/water. The solution was adjusted to pH 5 by the addition of 1N hydrochloric acid and extracted with methylene chloride. The crude product obtained after drying and evaporation of the organic phase was recrystallized from ethyl acetate/hexane and gave 1.4 g of p-[2-(1,2,3,4-tetrahydro-1,4,4-trimethyl-7-quinolinyl)propenyl]benzoic acid in the form of grey crystals, m.p. 194°-196° C.

The 1,2,3,4-tetrahydro-1,4,4-trimethyl-7-quinolinyl methyl ketone used as the starting material can be prepared as follows:

55.4 g of 3-bromoaniline were dissolved in 300 ml of hexane and treated with 76 ml of triethylamine. A solution of 40 g of 3,3-dimethylacrylyl chloride in 300 ml of hexane was added dropwise thereto while cooling with ice. After boiling at reflux for 3 hours, the mixture was poured on to ice/water and extracted with ether. The organic phase was washed with water, dried and evaporated. There was obtained a brown oil which was distilled in a high vacuum. The yield amounted to 51 g of N-(3-bromophenyl)-3,3-dimethyl-acrylamide (yellow oil), boiling point 146°-152° C./93 Pa.

28.7 g of powdered potassium hydroxide were suspended in 300 ml of dimethyl sulfoxide and a solution of 32.6 g of N-(3-bromophenyl)-3,3-dimethyl-acrylamide in 200 ml of dimethylsulfoxide (DMSO) was added dropwise thereto. The mixture was stirred at room temperature for 30 minutes and subsequently a solution of 27.5 g of methyl iodide in 150 ml of DMSO was added dropwise thereto. After 2.5 hours the mixture was poured on to 1 l of ice/water and extracted with ethyl acetate. The organic phase was washed repeatedly with water, dried and evaporated. The oily residue was distilled in a high vacuum. There were obtained 29.3 g of N-methyl-N-(3-bromophenyl)-3,3-dimethyl-acrylamide as a slightly yellow oil, boiling point 112°-114° C./67 Pa.

29.3 g of this oil were dissolved in 1 l of high-boiling petroleum ether. 30 g of Aluminum chloride were added thereto while stirring and the mixture was subsequently boiled at reflux for 3 hours. After cooling to 0°-5° C., 700 ml of 2N hydrochloric acid were slowly added dropwise thereto. The mixture was diluted with water and extracted with ether. The yellow-brown oil obtained after drying and evaporation of the solvent was a 1:1 mixture of 5-bromo- and 7-bromo-3,4-dihydro-1,4,4-trimethyl-2(1H)quinolinone. By column chromatography (silica gel, eluting agent hexane/ethyl acetate 9:1) there was first eluted the 7-bromo compound which crystallized from hexane, yield 4.2 g, melting point 92°-94° C.

14.2 g of the 7-bromo compound were dissolved in 300 ml of tetrahydrofuran and treated dropwise at 0° C. with a solution of 5.7 ml of borane-dimethyl sulfide complex (about 10 molar in excess dimethyl sulfide) in 250 ml of tetrahydrofuran. The reaction mixture was subsequently heated to reflux for 2.5 hours under argon, cooled to 0° C. and treated dropwise in succession with 700 ml of methanol and 300 ml of 6N hydrochloric acid. After 30 minutes, the mixture was evaporated in a water-jet vacuum. The liquid residue was treated with ice, made alkaline by the addition of ice-cold 3N sodium hydroxide solution and extracted with ether. After drying and evaporation of the solvent, there was obtained a yellowish oil which was distilled in a high vacuum and yielded 11.8 g of 7-bromo-1,2,3,4-tetrahydro-1,4,4-trimethylquinoline as a colorless oil, boiling point 124°-127° C./120 Pa. The compound solidified upon standing in a refrigerator.

2 g of Magnesium shavings were covered with 20 ml of tetrahydrofuran. A solution of 20.8 g of 7-bromo-1,2,3,4-tetrahydro-1,4,4-trimethylquinoline in 80 ml of tetrahydrofuran was added dropwise thereto at 55°-60° C. using an ultrasonics bath. Thereafter, the mixture was boiled at reflux for an additional 2 hours, cooled to 0° C. and a solution of 10 g of acetaldehyde in 80 ml of tetrahydrofuran was added dropwise thereto. After stirring at room temperature for 1 hour, the mixture was poured on to ice/saturated ammonium chloride solution and extracted with ether. The oil obtained after drying and evaporation of the solvent was filtered over a silica gel column (eluting agent hexane/ethyl acetate 9:1) and gave 14.5 g of 1,2,3,4-tetrahydro-α,1,4,4-tetramethyl-7-quinolinemethanol as a yellowish oil.

5.5 g of oxalyl chloride were dissolved in 50 ml of methylene chloride. At −60° C. there was added dropwise thereto a mixture of 6 ml of dimethyl sulfoxide and 35 ml of methylene chloride and, after 5 minutes, a solution of 8.5 g of the oil obtained in the previous step in 85 ml of methylene chloride. The mixture was stirred for an additional 15 minutes at −60° C. and there were then added dropwise thereto at this temperature 28 ml of trimethylamine. After removal of the cooling bath, the reaction mixture was stirred at room temperature for 2 hours. Subsequently, the mixture was poured on to ice and extracted with ether. The organic phase was washed with water, dried and evaporated. After filtration of the crude product over a short column (silica gel, eluting agent hexane/ethyl acetate=9:1) and crystallization from hexane, there were obtained 5 g of 1,2,3,4-tetrahydro-1,4,4-trimethyl-7-quinolinyl methyl ketone in the form of slightly yellowish crystals, m.p. 46°-48° C.

EXAMPLE 6

In analogy to Example 5, from 6.5 g of 6-acetyl-1,4-benzodioxane and 16.4 g of diethyl 4-carbethoxybenzyl)phosphonate, there were obtained, after filtration of the crude product over a column (silica gel, eluting agent hexane/ethyl acetate=9:1) and recrystallization from hexane/ethyl acetate, 7.3 g of ethyl p-[(E)-2-(1,4-benzodioxan-6-yl)propenyl]benzoate in the form of colorless crystals, m.p. 64°-66° C.

In analogy to Example 2, by hydrolysis of the thus-obtained ester, there was obtained p-[(E)-2-(1,4-benzodioxan-6-yl)propenyl]benzoic acid in the form of white crystals, m.p. 172°-173° C. (from ethyl acetate).

EXAMPLE 7

In analogy to Example 5, from 3.2 g of 6-acetyl-1,4-benzodithiane and 7.4 g of diethyl 4-carbethoxybenzyl)-phosphonate there were obtained, after filtration of the crude product over a column (silica gel, hexane/ethyl acetate=4:1) and recrystallization from hexane/ethyl acetate, 3.1 g of ethyl p-[(E)-2-(1,4-benzodithian-6-yl)propenyl]benzoate in the form of colorless crystals, m.p. 90°-92° C.

In analogy to Example 2, by hydrolysis of the thus-obtained ester with potassium hydroxide and recrystallization from ethyl acetate/hexane there is obtained p-[(E)-2-(1,4-benzodithian-6-yl)propenyl]benzoic acid in the form of white crystals, m.p. 236°-237° C.

EXAMPLE 8

15.1 g of α,2,2-trimethyl-1,3-benzodioxol-5-methanol were dissolved in 450 ml of acetonitrile and stirred at 50° C. for 3.5 hours with 24.6 g of triphenylphosphine hydrobromide. Thereafter, the mixture was evaporated in a vacuum. The residue was partitioned between 80 percent ethanol and hexane (in each case 600 ml three times); the aqueous-ethanol phase was evaporated in a vacuum, taken up in dichloromethane, dried over sodium sulfate, evaporated and dried in a vacuum: 39.6 g of [α-(2,2-dimethyl-1,3-benzodioxol-5-yl)ethyl]triphenylphosphonium bromide as a beige foam which did not crystallize, but which was practically pure according to thin-layer chromatography ($CH_2Cl_2$+5% MeOH).

12.5 g of this phosphonium salt and 4.7 g of methyl 4-formylbenzoate were boiled under reflux in 80 ml of 1,2-butylene oxide under argon for 16 hours. After cooling the product was partitioned between hexane (300 ml three times) and 70 percent ethanol (150 ml three times). The aqueous-ethanol phases were subsequently extracted three times with hexane and 10% ethyl acetate. After evaporation, there were obtained 5.46 g of hexane extract (A) and 1.23 g of hexane-ethyl acetate extract (B). Extract A yielded from hexane 2.39 g of crystalline, pure methyl p-[(E)-2-(2,2-dimethyl-1,3-benzodioxol-5-yl) propenyl]-benzoate, m.p. 72°–74° C. The mother liquors from extract A and extract B were chromatographed together on silica gel with hexane +5% ethyl acetate, whereby an additional 0.7 g of product of melting point 73°–75° C. was obtained.

EXAMPLE 9

A. 24.2 g of ethyl α-(diethoxyphosphinyl)-p-toluate were added under argon and while cooling with ice to 3.87 g of sodium hydride (50% in mineral oil) in 50 ml of dimethylformamide. The mixture was stirred at room temperature until the evolution of hydrogen had stopped. Thereafter, there was slowly added dropwise with ice/methanol cooling a solution of 15 g of 3,4-dihydro-3,3-dimethyl-2H-1,5-benzodithiepin-7-yl methyl ketone in 50 ml of dimethylformamide, whereby the internal temperature rose to 35° C. After an additional half hour, the reaction mixture was added to ice/sodium chloride and extracted with ether. The ethereal solution was washed with water, dried over sodium sulfate and evaporated under reduced pressure. Chromatography on silica gel (petroleum ether/ethyl acetate: 97/3) yielded 16.2 g of crude product which, after recrystallization from hexane, yielded 12.6 g of ethyl p[(E)-2-(3,4-dihydro-3,3,-dimethyl-2H-1,5-benzodithiepin-7-yl)propenyl]benzoate in the form of pale yellow crystals. M.p. 99° C.

The starting material was prepared as follows:

B. 15 g of dimercaptobenzene were slowly added dropwise while cooling to 5.55 g of sodium hydride (50% in mineral oil) in 150 ml of dimethyl sulfoxide, whereby the internal temperature was held between 15° and 23° C. Subsequently, the reaction mixture was stirred at room temperature for 1 hour and cooled with ice/methanol. Thereafter, 50 g of 2,2-dimethylpropanediol ditosylate in solid form were added in one portion and the reaction mixture was heated to 80° C. for 3 hours. Thereafter, the reaction mixture was cooled, poured on to ice, extracted with ether, the extract was washed with water and dried. After evaporation of the solvent, there was obtained a yellow oil which was chromatographed on silica gel (petroleum ether/ethyl acetate 99:1). There were obtained 14 g of 3,4-dihydro-3,3-dimethyl-2H-1,5-benzodithiepine as a colorless oil.

C. 13.3 g of 3,4-dihydro-3,3-dimethyl-2H-1,5-benzodithiepine were dissolved in 110 ml of ethylene chloride under argon and treated portionwise at −10° C. in succession with 10.1 ml of acetyl chloride and 19 g of aluminum chloride. Thereafter, the reaction mixture was stirred at room temperature for 2½ hours, poured on to ice and extracted with ether. The extract was washed with dilute sodium hydroxide solution and water, dried and evaporated to dryness. There were obtained 15.6 g of 3,4-dihydro-3,3-dimethyl-2H-1,5-benzodithiepin-7-yl methyl ketone in the form of brownish crystals.

EXAMPLE 10

In analogy to Example 9, from 3,4-dihydro-3,3-dimethyl-2H-1,5-benzodioxepin-7-yl methyl ketone there was obtained ethyl p-[(E)-2-(3,4-dihydro-3,3-dimethyl-2H-1,5-benzodioxepin-7-yl)propenyl]benzoate, m.p. 50°–51° C. The starting material was prepared in analogy to Example 9, paragraphs B and C, starting from pyrocatechol via 3,4-dihydro-3,3-dimethyl-2H-1,5-benzodioxepine.

EXAMPLE 11

In analogy to Example 9, from 3,4-dihydro-3-methyl-2H-1,5-benzodithiepin-7-yl methyl ketone, there was obtained ethyl p-[(E)-2-(3,4-dihydro-3-methyl-2H-1,5-benzodithiepin-7-yl)propenyl]benzoate, m.p. 68°–70° C. The starting material was prepared in analogy to Example 9, paragraphs B and C, via 3,4-dihydro-3-methyl-2H-1,5-benzodithiepine.

EXAMPLE 12

In analogy to Example 9, from 3,4-dihydro-2H-1,5-benzodithiepin-7-yl methyl ketone, there was obtained ethyl p-[(E)-2-(3,4-dihydro-2H-1,5-benzodithiepin-7-ylpropenyl]benzoate, m.p. 98°–99° C. The starting material was prepared in analogy to Example 9, paragraphs B and C, via 3,4-dihydro-2H-1,5-benzodithiepine.

EXAMPLE 13

A. 4.9 g of 2,3,4,5-tetrahydro-α-methyl-1-benzoxepine-8-methanol were dissolved in 50 ml of acetonitrile and treated with 13 g of triphenylphosphine hydrobromide. The reaction mixture was stirred at 40° C. for 24 hours. Thereafter, the majority of the solvent was removed under reduced pressure and the residue was partitioned between hexane and ethanol/water (8:2). The heavy phase was evaporated and dried, whereby 11.96 g of white phosphonium salt were obtained. 6.29 g of Phosphonium salt were dissolved in 13 ml of butylene oxide, treated with 2.6 g of ethyl 4-formylbenzoate and heated to reflux for 18 hours. Thereafter, the majority of the solvent was removed under reduced pressure and the residue was partitioned between hexane and ethanol/water (8:2). The light phase was dried over magnesium sulfate and evaporated. Chromatography on silica gel (petroleum ether/ethyl acetate (97:3)) and recrystallization from hexane yielded 1.4 g of ethyl p-[(E)-2-(2,3,4,5-tetrahydro-1-benzoxepin-8-yl)propenyl]benzoate, m.p. 71°–72° C.

The starting material was prepared as follows:

m-Bromophenol was reacted with γ-butyrolactone in analogy to Example 17, paragraphs B, C and D, to give 8-bromo-2,3,4,5-tetrahydro-1-benzoxepine.

B. 7.3 g of 8-bromo-2,3,4,5-tetrahydro-1-benzoxepine in 30 ml of absolute tetrahydrofuran were added under argon to 930 mg of Mg shavings and a granule of iodine. The reaction was initiated by the addition of a few drops of 1,2-dibromoethane and had finished after 2 hours. Thereafter, the reaction mixture was cooled to −10° C. and excess acetaldehyde was distilled into the reaction vessel. After 10 minutes, the mixture was hydrolyzed with saturated sodium bicarbonate (NaHCO$_3$) solution, extracted with ether, washed with water, dried and evaporated to dryness. Chromatography on silica gel (petroleum ether/ethyl acetate 3:1) yielded 4.93 g of 2,3,4,5-tetrahydro-α-methyl-1-benzoxepine-8-methanol as a colorless oil.

EXAMPLE 14

In analogy to Example 13, from 2,3,4,5-tetrahydro-α-methyl-3,3-dimethyl-2H-1-benzothiepine-8-methanol there was obtained methyl p-[(E)-2-(2,3,4,5-tetrahydro-3,3-dimethyl-2H-1-benzothiepin-8-yl)propenyl]benzoate, m.p. 82°–84° C. The starting material was prepared in analogy to Example 13, paragraph B, from 8-bromo-2,3,4,5-tetrahydro-1-benzothiepine.

EXAMPLE 15

In analogy to Example 13, from 2,3,4,5-tetrahydro-α-methyl-1-benzoxepine-7-methanol, there was obtained ethyl p-[(E)-2-(2,3,4,5-tetrahydro-1-benzoxepin-7-yl)propenyl]benzoate, m.p. 60°-61° C. The starting material was prepared as follows:

6.90 g of 2,3,4,5-tetrahydro-1-benzoxepin-7-yl methyl ketone in 60 ml of methanol were treated portionwise with 2.33 g of sodium borohydride (NaBH$_4$) at 0° C. while stirring. After a half hour the reaction mixture was poured on to ice, extracted with ether. The extract was washed with water, dried and evaporated. Chromatography on silica gel (petroleum ether/ethyl acetate 8:2) yielded 5.71 g of 2,3,4,5-tetrahydro-α-methyl-1-benzoxepine-7-methanol as a colorless oil.

The 2,3,4,5-tetrahydro-1-benzoxepin-7-yl methyl ketone can be obtained in analogy to Example 18, paragraph B, from 2,3,4,5-tetrahydro-1-benzoxepine by Friedel-Crafts reaction.

EXAMPLE 16

8.85 g of ethyl α-(diethoxyphosphinyl)-p-toluate were slowly added dropwise to 1.3 g of sodium hydride (50% in mineral oil) in 28 ml of dimethylformamide. The reaction mixture was stirred at room temperature until the evolution of hydrogen had finished. Thereafter, 4.2 g of 2,3,4,5-tetrahydro-3,3-dimethyl-benzothiepin-7-yl methyl ketone were added and the reaction mixture was stirred at room temperature for 2 hours. Thereafter, the mixture was poured on to ice/sodium chloride, extracted with ether, the ethereal solution was washed with water and dried and evaporated. Chromatography on silica gel (petroleum ether/ethyl acetate (95:5)) and recrystallization from hexane yielded ethyl p-[(E)-2-(2,3,4,5-tetrahydro-3,3-dimethyl-1-benzothiepin-7-yl)propenyl]benzoate of melting point 96°-97° C.

The starting material was prepared as follows:

17.8 g of 3,3-Dimethylglutaric anhydride were heated to reflux overnight in 130 ml of absolute ethanol. The reaction solution was brought to dryness (high vacuum), dissolved in 625 ml of benzene and stirred at room temperature for 2 hours with 2.1 ml of dimethylformamide and 6.25 ml of oxaxyl chloride. Thereafter, the reaction mixture is evaporated under reduced pressure. The thus-obtained acid chloride is dissolved in 80 ml of cyclohexane and added dropwise to a solution, boiling under reflux, of 20.4 g of 2-mercaptopyridine 1-oxide Na, 1.4 g of dimethylaminopyridine, 53.7 g of iodo form and 620 ml of cyclohexene. After 3 hours, the mixture is cooled, filtered and evaporated. After chromatography on silica gel (petroleum ether/ethyl acetate 9:1), there were obtained 14.8 g of ethyl 4-iodo-3,3-dimethylbutyrate. Reaction of this compound with sodium thiophenolate followed by hydrolysis yielded 4-phenylmercapto-3,3-dimethylbutyric acid which was converted via the acid chloride into 3,4-dihydro-3,3-dimethyl-1-benzothiepin-5(2H)-one. Reduction of the ketone in analogy to Example 17, paragraph D, and acetylation in analogy to Example 9, paragraph C, yielded 2,3,4,5-tetrahydro-3,3-dimethyl-1-benzothiepin-7-yl methyl ketone.

EXAMPLE 17

A. In analogy to Example 16, from 2,3,4,5-tetrahydro-1-benzothiepin-8-yl methyl ketone, there was obtained ethyl p-[(E)-2-(2,3,4,5-tetrahydro-1-benzothiepin-8-yl)propenyl]benzoate, m.p. 63°-64° C.

The starting material was prepared as follows:

B. 3.74 g of sodium were dissolved in 77 ml of absolute ethanol under argon. The solution was treated dropwise with 25 g of m-bromothiophenol and heated to reflux. Thereafter, 12.4 ml of γ-butyrolactone were added and the reaction mixture was heated to 110° C. for 5 hours. The separated carboxylic acid sodium salt was removed by filtration, washed with a small amount of ether and dissolved in 300 ml of water. The solution was acidified to pH 2 with 1N HCl while cooling with ice, the free carboxylic acid was extracted with ether, the ethereal solution was dried and evaporated. There were obtained 33.1 g of 4-(m-bromophenylmercapto)-butyric acid.

C. 33.1 g of the thus-obtained acid were heated to 120° C. with 275 g of polyphosphoric acid and 550 ml of o-xylene for 24 hours while stirring intensively. After cooling, the mixture was hydrolyzed with ice, diluted with water and extracted with ether. The organic phase was washed with water, dried and evaporated. Chromatography on silica gel (petroleum ether/ethyl acetate 9:1) yielded 22.1 g of 8-bromo-3,4-dihydro-1-benzothiepin-5(2H)-one as a brownish oil.

D. 15.6 g of 8-bromo-3,4-dihydro-1-benzothiepin-5(2H)-one were dissolved in 70 ml of diethylene glycol. The solution was treated with 6.55 ml of hydrazine hydrate and 7.5 g of solid potassium hydroxide and heated to 180°-190° C. under reflux for about 30 hours. After cooling, the mixture was poured on to ice and extracted with ether. The organic phase was washed with water, dried and evaporated. Chromatography on silica gel with petroleum ether yielded is 10.7 g of 8-bromo-2,3,4,5-tetrahydro-1-benzothiepine as a colorless oil.

E. The previously obtained bromide was converted into 2,3,4,5-tetrahydro-α-methyl-1-benzothiepine-8-methanol by a Grignard reaction in analogy to Example 13, last paragraph.

F. 7.80 g of 2,3,4,5-tetrahydro-α-methyl-1-benzothiepine-8-methanol were dissolved in 100 ml of methylene chloride, treated with 50 g of manganese dioxide (MnO$_2$) and the reaction mixture was stirred overnight. Thereafter, the mixture was filtered over a filter aid and the solution was evaporated. There were obtained 7.30 g of 2,3,4,5-tetrahydro-1-benzothiepin-8-yl methyl ketone as a colorless oil.

EXAMPLE 18

A. In analogy to Example 16, from 2,3,4,5-tetrahydro-5-methyl-1-benzothiepin-7-yl methyl ketone, there was obtained ethyl p-[(E)-2-(2,3,4,5-tetrahydro-5-methyl-1-benzothiepin-7-yl)propenyl]benzoate, m.p. 65° C. The starting material was prepared as follows:

B. 3.32 g of 2,3,4,5-tetrahydro-5-methyl-1-benzothiepine were added at 0° C. under argon to a solution of 2.64 ml of acetyl chloride and 4.96 g of aluminum chloride (AlCl$_3$) in 80 ml of ethylene chloride. The reaction mixture was stirred at room temperature overnight. Thereafter, it was poured on to ice, and extracted with ether. The organic phase was washed with 1N sodium hydroxide solution and water, dried and evaporated. There were obtained 3.66 g of 2,3,4,5-tetrahydr-5-methyl-1-benzothiepin-7-yl methyl ketone as a brownish oil.

EXAMPLE 19

In analogy to Example 16, from 2,3,4,5-tetrahydro-1-benzothiepin-7-yl methyl ketone, there was obtained ethyl p-[(E)-2-(2,3,4,5-tetrahydro-1-benzothiepin-7-yl)propenyl]benzoate, m.p. 98°–101° C. The starting material was prepared as follows:

3,4-Dihydro-1-benzothiepine (prepared from thiophenol in analogy to Example 17, paragraphs B and C) was converted analogously to Example 17, paragraph D, into 2,3,4,5-tetrahydro-1-benzothiepine from which the 2,3,4,5-tetrahydro-1-benzothiepin-7-yl methyl ketone was obtained by Friedel-Crafts reaction in analogy to Example 18, paragraph B.

EXAMPLE 20

In analogy to Example 16, from 2,3,4,5-tetrahydro-5,5-dimethyl-1-benzothiepin-7-yl methyl ketone, there was obtained ethyl p-[(E)-2-(2,3,4,5-tetrahydro-5,5-dimethyl-1-benzothiepin-7-yl)propenyl]benzoate, m.p. 65°–66° C. The starting material was prepared as follows:

A solution of 20.0 g of methoxymethyltriphenylphosphonium chloride in 60 ml of absolute tetrahydrofuran was treated dropwise at 0° C. under argon with 43 ml of 1.4N n-butyllithium in hexane. The mixture was stirred for ¼ hour. Thereafter, the mixture was treated with 8.02 g of 3,4-dihydro-1-benzothiepin-5(2H)-one in a small amount of tetrahydrofuran. After 5 minutes, the cooling bath was removed and the reaction mixture was stirred at room temperature for an additional 1½ hours. Thereafter, the reaction mixture was partitioned between petroleum ether and ethanol/water (8:2). The lighter phase was washed with water, dried over sodium sulfate and evaporated. There were obtained 11.8 g of crude product which were dissolved in 80 ml of tetrahydrofuran and treated under argon with 100 ml of 35% perchloric acid. The reaction mixture was stirred overnight, poured on to ice, extracted with ether, washed with 5% sodium carbonate solution, dried and evaporated. Chromatography on silica gel (petroleum ether/ethyl acetate 92:8) yielded 5.04 g of 2,3,4,5-tetrahydro-1-benzothiepine-5-carboxaldehyde as a colorless oil.

The thus-obtained product was dissolved in 50 ml of tert.-butanol and treated under argon with 3.37 g of potassium tert.-butylate. After 10 minutes at room temperature, the reaction solution was cooled to 0° C. and treated with 2.17 ml of methyl iodide. Thereafter, the reaction mixture was stirred at room temperature for 3 hours, poured on to ice, extracted with ether, washed with saturated sodium chloride solution and dried. After evaporation of the solvent and chromatography on silica gel (petroleum ether/ethyl acetate 92:8), there were obtained 3.29 g of 2,3,4,5-tetrahydro-5-methyl-1-benzothiepine-5-carboxaldehyde.

The thus-obtained product was dissolved in 20 ml of diethylene glycol and treated with 1.67 ml of hydrazine hydrate and 2.81 g of potassium hydroxide. The reaction mixture was heated slowly to 120° C., held at this temperature for a half hour and then heated to 180° C. After 3 hours, the mixture was cooled, partitioned between petroleum ether and water and the organic phase was washed with water. After drying and evaporation to dryness and chromatography (petroleum ether), there were obtained 2.4 g of 2,3,4,5-tetrahydro-5,5-dimethyl-1-benzothiepine as a colorless oil.

The thus-obtained product was converted into the 2,3,4,5-tetrahydro-5,5-dimethyl-1-benzothiepin-7-yl methyl ketone by a Friedel-Crafts reaction in analogy to Example 18, paragraph B.

EXAMPLE 21

4.0 g of ethyl p-[(E)-2-(2,3,4,5-tetrahydro-1-benzothiepin-7-yl)propenyl]benzoate in 30 ml of methylene chloride were treated with 6.05 g of m-chloroperbenzoic acid (85%) and held at about +5° C. for 24 hours. Thereafter, the mixture was diluted with methylene chloride, washed with bisulfite solution and sodium carbonate solution, dried and evaporated. Recrystallization from ethyl acetate/hexane yielded 3.7 g of ethyl p-[(E)-2-(2',3',4',5'-tetrahydro-1-benzothiepin-7'-yl)propenyl]benzoate 1',1'-dioxide as pale yellow crystals of melting point 147°–148° C.

In analogy, there were prepared:

Ethyl p-[(E)-2-(2',3',4',5'-tetrahydro-1-benzothiepin-8'-yl)propenyl]benzoate 1',1'-dioxide, m.p. 117°–119° C., ethyl p-[(E)-2-(2',3',4',5'-tetrahydro-5',5'-dimethyl-1-benzothiepin-7'-yl)propenyl]benzoate 1',1'-dioxide, m.p. 142°–143° C.

ethyl p-[(E)-2-(2',3',4',5'-tetrahydro-3',3'-dimethyl-1-benzothiepin-7'-yl)propenyl]benzoate 1',1'-dioxide, m.p. 155°–156° C.

ethyl p-[(E)-2-(3',4'-dihydro-3',3'-dimethyl-2'-H-1,5-benzodithiepin-7'-yl)propenyl]benzoate 1',1',5',5'-tetroxide, m.p. 175°–176° C.

EXAMPLE 22

A solution of 4.47 g of 2,3,4,5-tetrahydro-α-methyl-1-methyl-1H-1-benzazepine-7-methanol in 50 ml of acetonitrile was treated with 9.73 g of triphenylphosphine hydrobromide. The reaction mixture was stirred at 30° C. for 20 hours, concentrated and the residue was partitioned between hexane and aqueous ethanol (8:2). The lower phase was evaporated. The product was taken up in methylene chloride. The solution was dried and evaporated, whereby 12.3 g of phosphonium salt were obtained in the form of reddish crystals. 10.7 g of Phosphonium salt were suspended in 40 ml of absolute tetrahydrofuran under argon and deprotonized at 0° C. with 20.7 ml of 1.4M n-butyllithium solution. After 15 minutes, the dark red solution was treated with 4.76 g of methyl 4-formylbenzoate and stirred at room temperature for 1½ hours. Thereafter, the mixture was poured on to ice, extracted with ether, washed with water and dried and evaporated. Chromatography on silica gel (petroleum ether/ethyl acetate (95:5) and recrystallization from hexane/ethyl acetate yielded 3.6 g of methyl p-[(E)-2-(2,3,4,5-tetrahydro-1-methyl-1-benzazepin-7-yl)propenyl]benzoate in the form of pale yellow crystals of melting point 106° C.

The starting material was prepared as follows:

A. 45 ml of dimethylformamide were treated under an argon atmosphere with 16.2 ml of phosphorus oxychloride. After the reaction had faded away, 7.30 g of 2,3,4,5-tetrahydro-1-methyl-1H-1-benzazepine were added and the reaction mixture was stirred at 70° C. for 5 hours. Thereafter, the mixture was poured on to ice, made alkaline with sodium hydroxide solution, extracted with ether, washed with water, dried and evaporated. Chromatography on silica gel (petroleum ether/ethyl acetate (87:13)) yielded 4.38 g of 2,3,4,5-tetrahydro-1-methyl-1H-1-benzazepine-7-carboxaldehyde.

The Grignard reagent was prepared from 1.04 g of magnesium shavings and 2.30 ml of methyl iodide under argon in 40 ml of absolute ether. To this Grignard solution was slowly added dropwise at room temperature a solution of 4.38 g of 2,3,4,5-tetrahydro-1-methyl-1H-1-benzazepine-7-carboxaldehyde in 10 ml of ether. The reaction mixture was stirred for 2 hours. Thereafter, the mixture was hydrolyzed with saturated ammonium chloride solution, extracted with ether, washed with water and dried. After evaporation, there were obtained 4.47 g of 2,3,4,5-tetrahydro-α-methyl-1-methyl-1H-1-benzazepine-7-methanol as a yellow oil.

EXAMPLE 23

A solution of 1.2 g of ethyl p-[(E)-2-(2,3,4,5-tetrahydro-5-methyl-1-benzothiepin-7-yl)propenyl]benzoate in 30 ml of ethanol was treated with 5 ml of water which contained 0.8 g of sodium hyohoxide (NaOH). The reaction mixture was stirred at 35° C. overnight, poured on to ice, acidified with HCl and extracted with ether. The organic phase was washed with water, dried and concentrated. After recrystallization from ethyl acetate, there were obtained 885 mg of p-[(E)-2-(2,3,4,5-tetrahydro-5-methyl-1-benzothiepin-7-yl)-ropenyl]benzoic acid in the form of white crystals of melting point 186° C.

In an analogous manner, there were prepared:

p-[(E)-2-(3,4-Dihydro-3-methyl-2H-1,5-benzodithiepin-7-yl)propenyl]benzoic acid, m.p. 188°–189° C.

p-[(E)-2-(2',3',4',5'-tetrahydro-3',3'-dimethyl-1-benzothiepin-7'-yl)propenyl]benzoic acid 1',1'-dioxide, m.p. 250°–253° C.

p-[(E)-2-(2',3',4',5'-tetrahydro-1-benzothiepin-7'-yl)propenyl]benzoic acid 1',1'-dioxide, m.p. 240°–241° C., P-[(E)-2-(3,4-dihydro-3,3-dimethyl-2H-1,5-benzodithiepin-7'-yl)propenyl]benzoic acid, m.p. 212°–213° C., p-[(E)-2-(2',3',4',5'-tetrahydro-5',5'-dimethyl-1-benzothiepin-7'-yl)propenyl]benzoic acid 1',1'-dioxide, m.p. 225°–226° C.

p-[(E)-2-(2',3',4',5'-tetrahydro-1-benzothiepin-8'-yl)propenyl]benzoic acid 1',1'-dioxide, m.p. 219°–220° C., p-[(E)-2-(2,3,4,5-tetrahydro-1-benzothiepin-7-yl)propenyl]benzoic acid, m.p. 217°–218° C.

p-[(E)-2-(2,3,4,5-tetrahydro-5,5-dimethyl-1-benzothiepin-7-yl)propenyl]benzoic acid, m.p. 178°–179° C., p-[(E)-2-(3,4-dihydro-3,3-dimethyl-2H-1,5-benzodioxepin-7-yl)propenyl]benzoic acid, m.p. 198°–199° C., p-[(E)-2-(2,3,4,5-tetrahydro-1-benzothiepin-8-yl)propenyl]benzoic acid, m.p. 217°–218° C.

EXAMPLE 24

In analogy to Example 22, from 3,4-dihydro-α3,3-trimethyl-2H-1,5-benzodithiepin-7-ylmethanol, there was prepared methyl p-[(E)-2-(3,4-dihydro-3,3-dimethyl-2H-1,5-benzodithiepin-7-yl)propenyl]benzoate, m.p. 142°–143° C. The starting material was synthesized from 3,4-dihydro-3,3-dimethyl-2H-1,5-benzodithiepin-7-yl methyl ketone, prepared in Example 9(C), by reduction with sodium borohydride.

EXAMPLE 25

In analogy to Example 13 (paragraphs A and C), but using methyl 4-formylbenzoate in place of ethyl 4-formylbenzoate as the carbonyl component, there was prepared methyl p-[(E)-2-(2,3,4,5-tetrahydro-5-methyl-1-benzothiepin-8-yl)propenyl]benzoate, m.p. 88°–89° C.

The starting material was prepared as follows:

First, m-bromothiophenol was converted into 8-bromo3,4-dihydro-1-benzothiepin-5(2H)-one. This ketone was methylated with MeMgI in ether and the resulting tertiary alcohol was deoxygenated as follows: 22.85 g were placed in 250 ml of hexane under argon and treated in succession with 75.1 g of sodium iodide (NaI), 26.4 ml of acetonitrile and 63.5 ml of Me$_3$SiCl. The mixture was stirred at room temperature overnight, poured on to ice, extracted with ether, washed with bisulfite solution and water, dried and evaporated. Chromatography on silica gel with petroleum ether gave 18.1 g of 8-bromo-2,3,4,5-tetrahydro-5-methyl-1-benzothiepine as a pale yellow oil.

EXAMPLE 26

In analogy to Example 9 (paragraphs A and C), from 2,3,4,5-tetrahydro-3-methyl-1-benzothiepine, there was prepared ethyl p-[(E)-2-(2,3,4,5-tetrahydro-3-methyl-1-tienzothiepin-7-yl)propenyl]benzoate, m.p. 46°–49° C.

The starting material was prepared as follows:

Thiophenol was alkylated with 1-bromo-3-chloro-2-methylpropane in the presence of potassium carbonate (K$_2$CO$_3$) in acetone. The resulting primary chloride was lengthened by one carbon atom using KCN/18-crown-6 in acetonitrile. Basic hydrolysis, ring closure with polyphosphoric acid in analogy to Example 17(C) and Wolf-Kishner reduction according to Example 17(D) finally gave the required 2,3,4,5-tetrahydro-3-methyl-1-benzothiepine as a colorless oil.

EXAMPLE 27

In analogy to Example 20, from 3,4-dihydro-3-methyl-1-benzothiepin-5(2H)-one, there was prepared ethyl p-[(E)-2-(2,3,4,5-tetrahydro-3,5,5-trimethyl-2H-1-benzothiepin-7-yl)propenyl]benzoate, m.p. 99°–100° C.

EXAMPLE 28

In analogy to Example 16, from 2,3-dihydro-3,3-dimethyl-1,4-benzoxathiin-7-yl methyl ketone, there was prepared ethyl p-[(E)-2-(2,3-dihydro-3,3-dimethyl-1,4-benzoxathiin-7-yl)propenyl]benzoate, m.p. 69°–70° C.

The starting material was prepared as follows:

4.11 ml of 2-mercaptophenol and 27.4 g of finely powdered K$_2$CO$_3$ were placed in 40 ml of dimethyl formamide (DMF) and treated at 0° C. under an argon atmosphere with 4.08 ml of β-methallyl chloride. The mixture was left to react at room temperature for ½ hour, poured on to ice and extracted with ether. After washing with water, drying and evaporation there were obtained 7.80 g of a pale yellow oil which was dissolved in 60 ml of chloroform and, after the addition of 1 g of p-toluenesulfonic acid, heated to reflux overnight. Extractive working-up (ether) gave 6.96 g of tlc-uniform 2,3-dihydro-3,3-dimethyl-1,4-benzoxathien as a colorless oil. This was regioselectively acetylated in analogy to Example 18(B) to give 2,3-dihydro-3,3-dimethyl-1,4-benzoxathien-7-yl methyl ketone.

EXAMPLE 29

In analogy to Example 22, from 2,3,4,5-tetrahydro-1,3,3,5-tetramethyl-1H-1,5-benzodiazepine, there was prepared methyl p-[(E)-2-(2,3,4,5-tetrahydro-1,3,3,5-tetramethyl-1H-1,5-benzodiazepin-7-yl)propenyl]benzoate, m.p. 120°–121° C.

The starting material was prepared as follows:

120 mmol of NANH$_2$ (50% suspension in toluene) were placed in 40 ml of absolute tetrohydrofuran (THF) under argon. 40 mmol of t-BuOH in 10 ml of THF were added thereto and the mixture was stirred at 50° C. for 2 hours. Then, 40 mmol (5.2 g) of 1,3-diamino-N,N,2,2-tetramethylpropane, dissolved in 20 ml of THF, were added dropwise and the mixture was stirred at 50° C. for an additional hour. The mixture was cooled to 30° C., diluted with 200 ml of THF and 40 mmol (4.6 ml) of 1,2-dichlorobenzene were added thereto. After 18 hours, the mixture was worked-up extractively (ether). Rapid chromatography of the crude product on silica gel with hexane yielded 4.4 g of red-brown crystals.

EXAMPLE 30

4.2 g of 3,4-dihydro-3,3-dimethyl-2H-1,5-benzodioxepine-7-carboxylic acid were treated with 3 ml of SOCl$_2$ and heated under reflux for 1 hour. The excess reagent was evaporated in a vacuum and the resulting acid chloride was dried in a high vacuum. It was then dissolved in 70 ml of pyridine and there was slowly added dropwise thereto at 0° C. under an Argon atmosphere a solution of 4.05 g of ethyl p-aminobenzoate in 70 ml of pyridine. The mixture was left to react at room temperature for 2 hours, concentrated to ¼ of the volume and partitioned between ether and dilute HCl. The organic phase was washed thoroughly with water, dried and concentrated. The product thereby crystallized out. After cooling, suction filtration and drying, there were obtained 5.9 g of ethyl p-(3,4-dihydro-3,3-dimethyl-2H-1,5-benzodioxepine-7-carboxamido)benzoate as colorless crystals of m.p. 181°–182° C.

The starting material was prepared as follows:

A. 8.55 g of 3,4-dihydro-3,3-dimethyl-2H-1,5-benzodioxepine (see Example 10) were dissolved in 70 ml of methylene chloride (CH$_2$Cl$_2$) and treated at 0° C. under an Argon atmosphere with a solution of 8.0 g of Br$_2$ in 30 ml of CH$_2$Cl$_2$. The mixture was warmed to room temperature and left to react for 1 hour. It was then poured on to ice and extracted with ether. Washing with NaHCO$_3$ solution and water, drying and evaporation yielded 13.35 g of 7-bromo-3,4-dihydro-3,3-dimethyl-2H-1,5-benzodioxepine as a colorless oil which was 94.5% pure and which contained 4.7% of starting material; it was processed in the crude state.

B. The Grignard compound was prepared from 6.0 g of the thus-obtained bromide and 675 mg of Mg shavings under an Argon atmosphere in 25 ml of THF. The metallization had finished after 3 hours. The mixture was cooled to −10° C. and a vigorous stream of CO$_2$ was conducted in over 30 minutes. Ice was added cautiously thereto. The mixture was partitioned between dil. NaOH and ether, and the aqueous phase was adjusted to pH 1 with HCl and again extracted with ether. Washing with water, drying and evaporation yielded 4.2 g of 3,4-dihydro-3,3-dimethyl-2H-1,5-benzodioxepine-7-carboxylic acid as colorless crystals of m.p. 172°–173° C.

EXAMPLE 31

In analogy to Example 30, from 3,4-dihydro-3,3-dimethyl-2H-1,5-benzodithiepine-7-carboxylic acid chloride, there was prepared ethyl p-(3,4-dihydro-3,3-dimethyl-2H-1,5-benzodithiepine-7-carboxamido)benzoate, m.p. 180°–181° C.

The starting material was prepared in analogy to Example 30, paragraphs A and B, with Fe powder being used as the catalyst in the bromination and the acid chloride being prepared from the acid with oxalyl chloride.

EXAMPLE 32

In analogy to Example 30, from 2,3,4,5-tetrahydro-5-methyl-1-benzothiepine-8-carboxylic acid chloride, there was prepared ethyl p-(2,3,4,5-tetrahydro-5-methyl-1-benzothiepine-8-carboxamido)benzoate, m.p. 132°–133° C.

EXAMPLE 33

In analogy to Example 30, from 2,3,4,5-tetrahydro-1-benzothiepine-8-carboxylic acid chloride, there was prepared ethyl p-(2,3,4,5-tetrahydro-1-benzothiepine-8-carboxamido)benzoate, m.p. 100° C.

EXAMPLE 34

In analogy to Example 30, from 2,3,4,5-tetrahydro-1-benzothiepine-7-carboxylic acid chloride, there was prepared ethyl p-(2,3,4,5-tetrahydro-1-benzothiepine-7-carboxamido)benzoate, m.p. 145° C.

The starting material was prepared from 7-bromo-2,3,4,5-tetrahydro-1-benzothiepine in analogy to the procedure described in Example 30 and the latter compound was prepared starting from p-bromothiophenol in analogy to Example 17.

EXAMPLE 35

10.0 g of 3,4-dihydro-3,3-dimethyl-2H-1,5-benzodithiepin-7-yl methyl ketone (see Example 9) were dissolved in 100 ml of EtOH and treated portionwise with 2.0 g of NaBH$_4$. The mixture was left to react at room temperature overnight, and was diluted with water and extracted with ether. Washing with water, drying and evaporation yielded 10.0 g of secondary alcohol which was further processed in the crude state.

The secondary alcohol was dissolved in 150 ml of acetonitrile and treated with 19.5 g of triphenylphosphine hydrobromide. The mixture was stirred at 40° C. overnight and the majority of the solvent was then evaporated in a vacuum. The residue was partitioned between hexane and EtOH/H$_2$O=8/2, the heavy phase was evaporated and the residue was dissolved in CH$_2$Cl$_2$. Drying and evaporation gave a foam which was digested during several hours in hexane/ether=2/1; 20.6 g of colorless crystals thereby resulted.

4.64 g of the foregoing crystals were placed in 25 ml of THF and converted into the ylide at 0° C. with 5.8 ml of 1.6N nBuLi (hexane). The mixture was stirred at 0° C. for ¼ hour and 1.90 g of undiluted 4-(2-morpholinoethoxy)benzaldehyde were then added thereto. The mixture was left to warm to room temperature and was worked-up as follows after an additional 1 hour: the mixture was partitioned between EtOH/H$_2$O=8/2 and hexane/AcOEt=95/5 and the lighter phase was evaporated. Column chromatography on silica gel (ethyl acetate) of the thus-obtained crude product and crystallization from ether finally yielded 1.20 g of 4-[2-[p-[(E)-2-(3,4-dihydro-3,3-dimethyl-2H-1,5-benzodithiepin-7-yl)propenyl]phenoxy]ethyl]morpholine in the form of white crystals of m.p. 117°–118° C.

EXAMPLE 36

In analogy to Example 35, from 3,4-dihydro-3,3-dimethyl-2H-1,5-benzodioxepin-7-yl methyl ketone, there was prepared 4-[2-[p-[(E)-2-(3,4-dihydro-3,3- dimethyl-2H-1,5-benzodioxepin-7-yl)propenyl]phenoxy]ethyl]morpholine, m.p. 104°–105° C.

EXAMPLE 37

In analogy to Example 36, but using p-ethoxycarbonyloxybenzaldehyde as the carbonyl component, there was prepared p-[(E)-2-(3,4-dihydro-3,3-dimethyl-2H-1,5-benzodioxepin-7-yl)propenyl]phenyl ethyl carbonate.

590 mg of the foregoing carbonate were dissolved in 15 ml of ethanol and treated with 7 ml of water containing 700 mg of NaOH pellets. The mixture was stirred at 50° C. overnight, poured on to ice, extracted with ether, washed with water, dried and evaporated. Column chromatography on silica gel (petroleum ether/ethyl acetate=85/15) and subsequent crystallization from hexane/ether yielded 270 mg of p-[(E)-2-(3,4-dihydro-3,3-dimethyl-2H-1,5-benzodioxepin-7-yl)propenyl]phenol as white crystals of m.p. 70°–71° C.

EXAMPLE 38

8.30 g of 3,4-dihydro-2H-1,5-benzothiazepine hydrobromide were placed in 150 ml of THF and deprotonized with 48 ml of 1.55M nBuLi (hexane) under an Argon atmosphere at −10° C. After ¼ hour, 4.64 ml of Methyl iodide (MeI) were added dropwise to the yellow solution of the Li amide and the mixture was stirred for 1 hour. It was then poured on to ice, extracted with ether, washed with water, dried and evaporated. Column chromatography on silica gel (petroleum ether/ethyl acetate 96/4) yielded 5.70 g of 3,4-dihydro-5-methyl-2H-1,5-benzothiazepine as a colorless oil which was formulated as follows:

200 ml of DMF were placed under an Argon atmosphere and 11.3 ml of phosphorus oxychloride (POCl$_3$) were added dropwise thereto while cooling. The mixture was stirred at room temperature for ¼ hour, 5.70 g of the aromatic substrate were added thereto and the mixture was heated to 60°–70° C. for 1.5 hours. After cooling the mixture was poured on to ice, extracted with ether, washed with water, dried and evaporated. Crystallization from hexane/ethyl acetate yielded 5.20 g of aldehyde as yellow crystals of m.p. 56°–57° C. which was reacted as follows:

80 ml of ether, in which 5.20 g of the foregoing aldehyde had been dissolved, were slowly added dropwise at room temperature under an Argon atmosphere to an ethereal MeMgI solution which had been prepared from 968 mg of Mg shavings and 2.5 ml of MeI according to standard procedures. The mixture was stirred at room temperature for an additional 2 hours then hydrolyzed with ammonium chloride (NH$_4$Cl) solution and extracted with ether. Washing with water, drying and removal of the solvent in a vacuum yielded 5.50 g of secondary alcohol as an oil which was processed in the crude state.

The foregoing oil was placed in 40 ml of acetonitrile and treated with 10.1 g of triphenylphosphine hydrobromide. The mixture was stirred at 40° C. overnight and the clear solution was then concentrated in a vacuum. The residue was partitioned between hexane and EtOH/H$_2$O=8/2 and the heavy phase was evaporated. The thus-obtained crude product was dissolved in CH$_2$Cl$_2$, dried over Sodium sulfate (Na$_2$SO$_4$) and evaporated. Stirring for several hours in hexane/ether (2/1) finally yielded 14.4 g of crystalline phosphonium salt.

These 14.4 g of phosphonium salt were placed in 60 ml of THF under an Argon atmosphere and converted into the deep red ylide at 0° C. with 22.1 ml of 1.5M nBuLi (hexane). After 5 minutes, 4.65 g of methyl 4-formyl-benzoate were added thereto as the solid and the cooling bath was subsequently removed. After 1.5 hours, the mixture was poured on to ice, extracted with ether, washed with water, dried and evaporated. Careful chromatography on silica gel (petroleum ether/ethyl acetate 92/8) and recrystallization from hexane/ethyl acetate finally yielded 2.65 g of methyl p-[(E)-2-(3,4-dihydro-5-methyl-2H-1,5-benzothiazepin-8-yl)propenyl]benzoate as yellow crystals of m.p. 97°–98° C.

EXAMPLE 39

In analogy to Example 38, there was prepared methyl p-[(E)-2-(3,4-dihydro-3,5-dimethyl-2H-1,5-benzothiazepin-8-yl)propenyl]benzoate, m.p. 101°–102° C.

The starting material was synthesized as follows:

18.8 g of 2-aminothiophenol were placed in 75 ml of acetone and treated at 0° C. with 41.6 g of powdered K$_2$CO$_3$ and 18.2 ml of 1-bromo-3-chloro-2-methylpropane, whereby a strong exothermic reaction set in immediately. After 2 hours the mixture was poured on to ice, extracted with ether, washed with water, dried and evaporated. There were obtained 32.0 g of S-alkylated product which was dissolved in 80 ml of acetone. The solution was treated with 111 g of sodium iodide (NaI) and heated (oil bath 90° C.) for 3 days. The mixture was cooled, poured on to ice, made basic with sodium hydroxide solution, extracted with ether, washed with water, dried and evaporated. Column chromatography on silica gel (petroleum ether/ethyl acetate 95/5) yielded 10.0 g of 3,4-dihydro-3-methyl-2H-1,5-benzothiazepine as a colorless oil, although contaminated with 14% of an unknown compound. A complete purification was carried out at the aldehyde stage.

The further reaction was effected as in Example 38 by formylation, reaction with methyl magnesium iodide and preparation of the phosphonium salt.

EXAMPLE 40

In analogy to Example 35, but using 4-(2-dimethylaminoethoxy)benzaldehyde as the carbonyl component, there was obtained N,N-dimethyl-2-[p-[(E)-2-(3,4-dihydro-3,3-dimethyl-2H-1,5-benzodithiepin-7-yl)propenyl]phenoxy]ethylamine, m.p. 46°–47° C.

EXAMPLE 41

In analogy to Example 30, from 2,3,4,5-tetrahydro-3-methyl-1-benzothiepine-7-carboxylic acid chloride-1,1-dioxide, there was obtained ethyl p-(2,3,4,5-tetrahydro-3-methyl-1-benzothiepine-7-carboxamido)benzoate 1,1-dioxide, m.p. 181°–182° C.

The starting material was prepared as follows:

2,3,4,5-Tetrahydro-3-methyl-1-benzothiepin-7-yl methyl ketone was oxidized in analogy to Example 21 to give the sulfone and this was subjected to a hypochlorite degradation.

23.6 g of Ca(OCl)$_2$ were placed in 88 ml of water and treated with 16.6 g of K$_2$CO$_3$ and 4.77 g of NaOH dissolved in 44 ml of water. The mixture was stirred for 15 minutes. The precipitate was removed by filtration and the filtrate was heated to 50° C. Thereafter, 11.4 g of 2,3,4,5-tetrahydro-3-methyl-1-benzothiepin-7-yl methyl ketone 1,1-dioxide were added, whereby the temperature rose to 90° C. as a consequence of the heat of reaction. After 2 hours, the mixture was cooled, filtered and the filtrate was adjusted to pH 1 with 3N HCl while flushing with Argon (evolution of Cl₂). The separated acid was removed by filtration under suction, washed with water and dried; yield 9.60 g, m.p. 209°–212° C.

EXAMPLE 42

In an analogous manner to Example 23, there were prepared:

p-[(E)-2-(2,3-Dihydro-3,3-dimethyl-1,4-benzoxathiin-7-yl)propenyl]benzoic acid, m.p. 217°–218° C.;

p-[(E)-2-(3,4-dihydro-2H-1,5-benzodithiepin-7-yl)propenyl]benzoic acid, m.p. 202°–203° C.;

p-[(E)-2-(2,3,4,5-tetrahydro-3-methyl-1-benzothiepin-7-yl)propenyl]benzoic acid, m.p. 195°–196° C.;

p-[(E)-2-(3,4-dihydro-3,3-dimethyl-2H-1,5-benzodioxepin-7-yl)propenyl]benzoic acid, m.p. 198°–199° C.;

p-[(E)-2-(2,3,4,5-tetrahydro-5,5-dimethyl-1-benzothiepin-7-yl)propenyl]benzoic acid, m.p. 178°–179° C.;

p-[(E)-2-(3,4-dihydro-5-methyl-2H-1,5-benzothiazepin-8-yl)propenyl]benzoic acid, m.p. 197°–198° C.; p-[(E)-2-(2,3,4,5-tetrahydro-3,5,5-trimethyl-2H-1-benzothiepin-7-yl)propenyl]benzoic acid, m.p. 175°–176° C.; and p-[(E)-2-(3,4-dihydro-3,5-dimethyl-2H-1,5-benzothiazepin-8-yl)propenyl]benzoic acid, m.p. 213°–214° C.

EXAMPLE 43

1.20 g of ethyl p-(2,3,4,5-tetrahydro-1-benzothiepine-8-carboxamido)benzoate were dissolved in 40 ml of ethanol and treated with 14 ml of water containing 1.40 g of NaOH. The mixture was stirred at room temperature overnight, poured on to ice and acidified with conc. HCl. The mixture was then extracted twice with ethyl acetate, washed with is water, dried and evaporated. Recrystallization from ethyl acetate gave 925 mg of p-(2,3,4,5-tetrahydro-1-benzothiepine-8-carboxamido)benzoic acid as colorless crystals of m.p. 261°–262° C.

EXAMPLE 44

28.9 g of aluminum chloride were added portionwise at 0° C. to 16.8 ml of acetyl chloride in 360 ml of methylene chloride. After an additional 30 minutes at 0° C., a solution of 35.9 g of 2,2-dimethyl-1,3-benzodithiol in 180 ml of methylene chloride was slowly added dropwise and the mixture was stirred at 0° C. for an additional 12 hours and thereafter at 20° C. for 5 hours. Thereafter, the mixture was poured on to ice, extracted with methylene chloride and the extracts were washed neutral with dilute sodium hydroxide solution and water, dried over sodium sulfate and evaporated. After recrystallization from methanol/ water, there were obtained 41.8 g of 2,2-dimethyl-1,3-benzodithiol-5-yl methyl ketone, melting point 75°–76° C. Then, 41.8 g of this ketone were dissolved in 1 l of ethanol, cooled to 0° C. and 7 g of sodium borohydride were added portionwise. Thereafter, the mixture was stirred at 20° C. for 3 hours, evaporated in a vacuum to a large extent, 200 ml of water were added, the mixture was adjusted slowly to pH 4 with 1N sulfuric acid while cooling and extracted three times with ether. The extracts were washed with water, dried and evaporated, and 42.6 g of α,2,2-trimethyl-1,3-benzodithiol-5-methanol were obtained. Thereafter, 39.5 g of this alcohol were reacted with 65.9 g of triphenylphosphine hydrobromide in 500 ml of acetonitrile and worked-up as described in Example 8 and 96.3 g of [1-(2,2-dimethyl-1,3-benzodithiol-5-yl)ethyl]triphenylphosphonium bromide were obtained. Then, 17.0 g of this phosphonium salt were reacted with methyl 4-formyl-benzoate in analogy to Example 8. After working-up and recrystallization from ethyl acetate/hexane, there were obtained 4.9 g of methyl p-[(E)-2-(2,2-dimethyl-1,3-benzo-dithiol-5-yl)propenyl]benzoate in the form of colorless crystals, melting point 86°–87° C.

EXAMPLE 45

6.6 g of [1-(2,2-dimethyl-1,3-benzodithiol-5-yl)ethyl]triphenylphosphonium bromide were dissolved in 40 ml of tetrahydrofuran and treated slowly at 0° C. with 9 ml of a 1.5 molar solution of n-butyllithium in hexane. After 40 minutes, 3.5 g of 4-(2-morpholinoethoxy)benzaldehyde in 10 ml of tetrahydrofuran were added dropwise to the dark red solution and the mixture was stirred at 20° C. for 16 hours. The mixture was then poured on to ice and extracted with ethyl acetate. The combined extracts were washed with water, dried and evaporated. After chromatography (silica gel, eluting agent ethyl acetate) and crystallization from ether/hexane, there were obtained 1.8 g of 4-[2-[p-[(E)-2-(2,2-dimethyl-1,3-benzodithiol-5-yl)propenyl]phenoxy]ethyl]morpholine in the form of colorless crystals, melting point 90°–91° C.

EXAMPLE 46

In analogy to Example 45, by reacting [1-(2,2-dimethyl-1,3-benzodithiol-5-yl)ethyl]triphenylphosphonium bromide with benzaldehyde, there was obtained 2,2-dimethyl-5-[(E)-α-methylstyryl]-1,3-benzodithiol, melting point 57°–58° C.

EXAMPLE 47

In analogy to Example 45, by reacting [1-(2,2-dimethyl-1,3-benzodithiol-5-yl)ethyl]triphenylphosphonium bromide with ethyl 4-formylphenyl carbonate, there was obtained ethyl p-[(E)-2-(2,2-dimethyl-1,3-benzodithiol-5-yl)propenyl]phenyl carbonate, melting point 93°–94° C. Hydrolysis of this compound with aqueous potassium hydroxide in ethanol gave p-[(E)-2-(2,2-dimethyl-1,3-benzodithiol-5-yl)propenyl]phenol, melting point 123°–124° C.

EXAMPLE 48

In analogy to Example 23, by hydrolyzing methyl p-[(E)-2-(2,2-dimethyl-1,3-benzodithiol-5-yl)propenyl]benzoate, there was obtained p-[(E)-2-(2,2-dimethyl-1,3-benzodithiol-5-yl)propenyl]benzoic acid, melting point 204°–206° C.

EXAMPLE 49

16.5 g of [1-(4,4-dimethyl-6-chromanyl)ethyl]triphenylphosphonium bromide and 3 g of benzaldehyde were heated under reflux in 100 ml of butylene oxide for 20 hours. The reaction mixture obtained was poured into a methanol/water mixture (6:4) and extracted with hexane. After drying and evaporating the organic phase the crude product was chromatographed (silica gel, eluting agent hexane) and recrystallized from hexane. There were obtained 1.5 g of 3,4-dihydro-4,4-dimethyl-6-[(E)-α-methylstyryl]-2H-1-benzopyran in the form of colorless crystals, melting point 64°–65° C.

EXAMPLE 50

1.1 g of sodium hydride (50% suspension in mineral oil) were washed twice with pentane, dried and suspended in 20 ml of dimethylformamide. A solution of 10.9 g of [1-(4,4-dimethyl-6-thiochromanyl)ethyl]triphenylphosphonium bromide in 60 ml of dimethylformamide was added dropwise thereto at 0° C. After stirring at 0° C. for 1 hour, a solution of 2.1 g of benzaldehyde in 20 ml of dimethylformamide was added dropwise and the mixture was stirred at room temperature for an additional 3 hours. After working-up in analogy to Example 49, the crude product was recrystallized from hexane and gave 3.3 g of 3,4-dihydro-4,4-dimethyl-6-(α-methylstyryl)-2H-1-benzothiopyran, melting point 81°–83° C.

EXAMPLE 51

Oxidation of the compound obtained according to Example 50 with m-chloroperbenzoic acid in analogy to Example 4, gave 3,4-dihydro-4,4-dimethyl-6-(α-methylstyryl)-2H-1-benzothiopyran 1,1-dioxide, melting point 156°–158° C.

EXAMPLE 52

5.1 g of [1-(1,2,3,4-tetrahydro-1,4,4-trimethyl-6-quinolinyl)ethyl]triphenylphosphonium bromide were suspended in 40 ml of tetrahydrofuran and treated at −20° C. with 5.9 ml of a 1.6 molar solution of n-butyllithium in hexane. After stirring at −20° C. for 1 hour, 1 g of benzaldehyde was added thereto and the mixture was stirred at room temperature for an additional 1 hour. After working-up in analogy to Example 49 and recrystallization from hexane, there were obtained 1.2 g of 1,2,3,4-tetrahydro-1,4,4-trimethyl-6-(α-methylstyryl)quinoline, melting point 69°–71° C.

EXAMPLE 53

33 g of [1-(3,4-dihydro-4,4-dimethyl-2H-1-benzothiopyran-7-yl)ethyl]triphenylphosphonium bromide and 6.5 g of benzaldehyde were heated under reflux in 300 ml of butylene oxide for 16 hours. After working-up in analogy to Example 49 and recrystallization from hexane, there were obtained 7.9 g of 3,4-dihydro-4,4-dimethyl-7-(α-methylstyryl)-2H-1-benzothiopyran, melting point 67°–69° C.

EXAMPLE 54

Oxidation of the compound obtained according to Example 53 with m-chloroperbenzoic acid, in analogy to Example 4 gave 3,4-dihydro-4,4-dimethyl-7-(α-methylstyryl)-2H-1-benzothiopyran 1,1-dioxide, melting point 148°–150° C. (from ethyl acetate).

EXAMPLE 55

1.7 g of magnesium shavings were covered with 10 ml of ether. A solution of 7.7 g of benzyl chloride in 80 ml of ether was added dropwise thereto under slight reflux and the mixture was subsequently held at boiling for an additional hour until the magnesium had dissolved completely. After cooling to room temperature, a solution of 7 g of 3,4-dihydro-4,4-dimethyl-7-acetyl-2H-1-benzopyran in 50 ml of ether was added dropwise and the reaction mixture was heated under reflux for an additional 2.5 hours. After cooling, the mixture was poured on to ice/2N hydrochloric acid and extracted with ether. The organic phase was washed with water and dilute sodium bicarbonate solution, dried and evaporated. The thus-obtained slightly yellow oil was dissolved in 10 ml of acetic acid and, after the addition of 0.5 g of p-toluenesulfonic acid, heated under reflux for 2 hours. The reaction solution obtained was diluted with water and extracted several times with ether. The combined extracts were diluted with water, washed with sodium bicarbonate solution and water, dried and evaporated. The crude product was chromatographed (silica gel, eluting agent hexane/0.5% ethyl acetate) and recrystallized from hexane. There were obtained 4.8 g of 3,4-dihydro-4,4-dimethyl-7-(α-methylstyryl)-2H-1-benzopyran, melting point 44°–46° C.

EXAMPLE 56

In analogy to Example 55, by a Grignard reaction of benzylmagnesium chloride with 3,4-dihydro-1,4,4-trimethyl-7-acetylquinoline, there was prepared 3,4-dihydro-1,4,4-trimethyl-7-(α-methylstyryl)quinoline, melting point 66°–68° C. (from hexane).

EXAMPLE 57

A solution of 14.2 g of 7-bromo-3,4-dihydro-4,4-dimethyl-2H-1-benzopyran and 1.1 g of 1,2-dibromoethane in 80 ml of tetrahydrofuran was added dropwise using a heatable ultrasonics bath, to a suspension, boiling under reflux, of 1.6 g of magnesium shavings in 20 ml of tetrahydrofuran. After heating under reflux for an additional 2 hours, the reaction mixture was cooled to 0° C. and a strong stream of carbon dioxide gas was conducted in (about 1 hour). Thereafter, the mixture was poured on to ice, acidified with 2N hydrochloric acid and extracted with ethyl acetate. The organic extracts were washed with water, dried and evaporated. After recrystallization from ethyl acetate/hexane, there were obtained 5.3 g of 3,4-dihydro-4,4-dimethyl-2H-1-benzopyran-7-carboxylic acid, melting point 173°–174° C.

1.4 g of the thus-obtained acid were heated under reflux for 1 hour with 20 ml of thionyl chloride. The excess thionyl chloride was subsequently distilled off in a water-jet vacuum. The residual acid chloride was dissolved in 20 ml of tetrahydrofuran and added dropwise at room temperature to a solution of 1.2 g of methyl 4-amino-benzoate in 30 ml of pyridine. After stirring for 1 hour, the mixture was poured on to ice/water and extracted with ethyl acetate. The organic extracts were washed twice with 2N hydrochloric acid and water, dried and evaporated. After filtration of the crude product over a silica gel column (eluting agent hexane/ethyl acetate 2:1), there were obtained 2.4 g of ethyl p-(3,4-dihydro-4,4-dimethyl-2H-1-benzopyran-7-carboxamido)benzoate as a colorless oil.

The ethyl ester was dissolved in 20 ml of ethanol and treated with a solution of 1.9 g of potassium hydroxide in 10 ml of water. After stirring at 40° C. for 1 hour, the mixture was poured on to ice, acidified with cold 2N hydrochloric acid and extracted with ethyl acetate. The organic extracts were washed with water, dried and evaporated. After recrystallization of the crude product from ethyl acetate/hexane, there were obtained 2.1 g of p-(3,4-dihydro-4,4-dimethyl-2H-1-benzopyran-7-carboxamido)benzoic acid in the form of colorless crystals, melting point 279°–281° C.

EXAMPLE 58

11 g of 7-bromo-3,4-dihydro-4,4-dimethyl-2H-1-benzothiopyran were dissolved in a mixture of 100 ml of ether and 10 ml of tetrahydrofuran and treated at −78° C. with 33 ml of a 1.6 molar solution of n-butyllithium in hexane. The reaction solution was held at −50° C. for 15 minutes, again cooled to −78° C. and gassed with carbon dioxide for 2 hours. Thereafter, the mixture was poured on to ice, acidified with 6N hydrochloric acid and extracted with ethyl acetate. The organic phases were washed with water, dried and evaporated. After recrystallization of the crude product from ethyl acetate/hexane, there were obtained 4.6 g of 3,4-dihydro-4,4-dimethyl-2H-1-benzothiopyran-7-carboxylic acid, melting point 202°–204° C.

5.4 g of this acid were treated with 30 ml of oxalyl chloride and heated at reflux for 1 hour. After evaporation of the excess acid chloride, the residue was dissolved in 50 ml of tetrahydrofuran and added dropwise at room temperature to a solution of 3.6 g of ethyl 4-amino-benzoate and 70 ml of pyridine. Working-up in analogy to Example 57 and recrystallization from ethyl acetate/hexane gave 6.6 g of ethyl p-(3,4-dihydro-4,4-dimethyl-2H-1-benzothiopyran-7-carboxamido)benzoate in the form of white crystals, melting point 148°–150° C.

Hydrolysis of the foregoing ester with potassium hydroxide/ethanol/water in analogy to Example 57 gave p-(3,4-dihydro-4,4-dimethyl-2H-1-benzothiopyran-7-carboxamido)benzoic acid, melting point 274°–276° C.

EXAMPLE 59

Oxidation of 4 g of ethyl p-(3,4-dihydro-4,4-dimethyl-2H-1-benzothiopyran-7-carboxamido)benzoate with m-chloroperbenzoic acid in analogy to Example 4 gave, after recrystallization from ethyl acetate/hexane, 4.2 g of ethyl p-(3,4-dihydro-4,4-dimethyl-2H-1-benzothiopyran-7-carboxamido)benzoate 1,1-dioxide, melting point 208°–210° C. Hydrolysis of this compound in analogy to Example 57, gave p-(3,4-dihydro-4,4-dimethyl-2H-1-benzothiopyran-7-carboxamido)benzoic acid 1,1-dioxide, melting point 314°–316° C.

EXAMPLE 60

2.7 g of 7-bromo-1,2,3,4-tetrahydro-1,4,4-trimethylquinoline were dissolved in 100 ml of ether and treated at −78° C. with 27 ml of n-butyllithium (1.6 mol in hexane). After stirring at −40° C. for 3 hours, carbon dioxide gas was conducted in during 1.5 hours. The working-up was effected in analogy to Example 57 and gave, after recrystallization from ethyl acetate/hexane, 1.9 g of 1,2,3,4-tetrahydro-1,4,4-trimethyl-7-quinolinecarboxylic acid, melting point 166°–168° C.

1.4 g of this acid were converted with oxalyl chloride in analogy to Example 58 into the acid chloride which was reacted with 1.1 g of ethyl 4-amino-benzoate in 100 ml of pyridine to give 1.7 g of ethyl p-(1,2,3,4-tetrahydro-1,4,4-trimethyl-7-quinolinecarboxamido)benzoate, melting point 118°–119° C. (from ether/hexane).

Hydrolysis of this ester with potassium hydroxide/water/ethanol gave, after recrystallization from ethyl acetate/hexane, p-(1,2,3,4-tetrahydro-1,4,4-trimethyl-7-quinolinecarboxamido)benzoic acid, melting point 279° C. (decomposition).

EXAMPLE 61

In analogy to Example 60, from 7-bromo-1-decyl-1,2,3,4-tetrahydro-4,4-dimethylquinoline, there was prepared ethyl p-(1-decyl-1,2,3,4-tetrahydro-4,4-dimethyl-7-quinolinecarboxamido)benzoate, melting point 105°–106° C. (from ethyl acetate/hexane).

Hydrolysis of the ester in analogy to Example 57 yielded p-(1-decyl-1,2,3,4-tetrahydro-4,4-dimethyl-7-quinolinecarboxamido)benzoic acid, melting point 194°–196° C. (from ethyl acetate/hexane).

EXAMPLE 62

3.7 g of 1,4-benzodioxane-6-carboxylic acid were treated with 50 ml of thionyl chloride. After boiling at reflux for 1 hour, the excess thionyl chloride was evaporated. The residue was dissolved in 15 ml of tetrahydrofuran and added dropwise at room temperature to a solution of 3.3 g of ethyl 4-amino-benzoate in 80 ml of pyridine. After stirring for 2 hours, the mixture was poured on to ice/water and extracted with ethyl acetate. The organic phases were washed with 2N hydrochloric acid and water, dried and evaporated. After recrystallization from ethyl acetate/hexane, there were obtained 5.6 g of ethyl p-(1,4-benzodioxane-6-carboxamido)benzoate, melting point 134°–136° C.

Hydrolysis of this ester with potassium hydroxide/water/ethanol at 50° C. during 2 hours yielded p-(1,4-benzodioxane-6-carboxamido)benzoic acid, melting point 278°–280° C.

EXAMPLE 63

32 g of [1-(4,4-dimethyl-6-thiochromanyl)ethyl]triphenylphosphonium bromide were suspended in 130 ml of tetrahydrofuran and treated at 0° C. with 37 ml of n-butyllithium (1.6 molar in hexane). After stirring at 0° C. for 45 minutes, a solution of 10 g of 4-(2-dimethylaminoethoxy)benzaldehyde in 60 ml of tetrahydrofuran was added dropwise to the orange reaction mixture. The mixture was stirred at room temperature for an additional 1 hour, poured on to ice/water and extracted with ether. The organic phases were washed with water, dried and evaporated. After filtration of the crude product over neutral Alox (eluting agent ether) and recrystallization from hexane/ether, there were obtained 8.7 g of 2-[p-[(E)-2-(3,4-dihydro-4,4-dimethyl-2H-1-benzothiopyran-6-yl)propenyl]phenoxy]-N,N-dimethylethylamine, melting point 81°–82° C.

EXAMPLE 64

In analogy to Example 63, by reacting [1-(4,4-dimethyl-6-thiochromanyl)ethyl]triphenylphosphonium bromide with 4-(2-morpholinoethoxy)benzaldehyde in a Wittig reaction, there was prepared 4-[2-[p-[(E)-2-(3,4-dihydro-4,4-dimethyl-2H-1-benzothiopyran-6-yl)propenyl]phenoxy]ethyl]morpholine, melting point 86°–88° C. (from ether/hexane).

EXAMPLE 65

In analogy to Example 63, by reacting [1-(4,4-dimethyl-6-thiochromanyl)ethyl]triphenylphosphonium bromide 1,1-dioxide with 4-(2-dimethylaminoethoxy)benzaldehyde in a Wittig reaction, there was prepared 2-[p-[(E)-2-(3,4-dihydro-4,4-dimethyl-2H-1-benzothiopyran-6-yl)propenyl]phenoxy]-N,N-dimethylethylamine 1,1-dioxide, melting point 121°–122° C. (from ether/hexane).

EXAMPLE 66

In analogy to Example 63, by reacting [1-(4,4-dimethyl-6-chromanyl)ethyl]triphenylphosphonium bromide with 4-(2-dimethylaminoethoxy)benzaldehyde in a Wittig reaction, there was prepared 2-[p-[(E)-2-(3,4-dihydro-4,4-dimethyl-2H-1-benzopyran-6-yl)propenyl]phenoxy]-N,N-dimethylethylamine as a colorless oil.

EXAMPLE 67

2.5 ml of Methyl iodide were dissolved in 30 ml of ether and added dropwise under slight reflux to a suspension of 972 mg of magnesium shavings in 15 ml of ether. After all of the magnesium had dissolved a solution of 6.2 g of 1,2,3,4-tetrahydro-1,4-dimethyl-6-formylquinoxaline in 15 ml of ether was added dropwise while cooling slightly. After stirring at room temperature for 3 hours, an aqueous solution of ammonium chloride was added dropwise while cooling with ice and the reaction mixture was subsequently extracted with ether. After drying and evaporation of the organic extracts, the crude product was purified further by flash chromatography (silica gel, eluting agent hexane/ethyl acetate 1:1) and gave 6 g of a yellow oil.

This oil was dissolved in 300 ml of acetonitrile and 11 g of triphenylphosphine hydrobromide were added. After stirring for 16 hours, the mixture was evaporated. The residue was dissolved in 300 ml of ethanol/water (8:2) and extracted several times with hexane. The aqueous phase was evaporated, dissolved in methylene chloride, again evaporated, again taken up with methylene chloride, dried over sodium sulfate and evaporated. There were obtained 12.4 g of a greenish, extremely hygroscopic phosphonium salt as an amorphous powder.

10.3 g of this phosphonium salt were dissolved in 200 ml of tetrahydrofuran and treated at $-78°$ C. with 19 ml of a 1.6 molar solution of n-butyllithium in hexane. After stirring at $-78°$ C. for 1 hour, a solution of 5.1 g of methyl 4-formyl-benzoate in 30 ml of tetrahydrofuran was added dropwise thereto. The mixture was left to come to room temperature and was stirred for an additional 2 hours. After working-up in analogy to Example 3, the crude product was purified by flash chromatography (silica gel, eluting agent hexane/ethyl acetate=4:1) and recrystallized from hexane. There were obtained 3.6 g of methyl p-[(E)-2-(1,2,3,4-tetrahydro-1,4-dimethyl-6-quinoxalinyl)propenyl]-benzoate in the form of yellow crystals, melting point 91°–93° C.

600 mg of this ester were converted into the free acid by reaction with a solution of 1.5 g of potassium hydroxide in 25 ml of ethanol and 10 ml of water at 50° C. during 4 hours. After recrystallization from ethyl acetate/hexane, there were obtained 450 mg of p-[(E)-2-(1,2,3,4-tetrahydro-1,4-dimethyl-6-quinoxalinyl)-propenyl]benzoic acid in the form of orange crystals, melting point 203°–205° C.

EXAMPLE 68

In analogy to Example 43, there were prepared:
p-(2,3,4,5-Tetrahydro-5-methyl-1-benzothiepine-8-carboxamido)benzoic acid, m.p. >270° C.;

p-(3,4-dihydro-3,3-dimethyl-2H-1,5-benzodithiepine-7-carboxamido)benzoic acid, m.p. >250° C.;

p-(3,4-dihydro-3,3-dimethyl-2H-1,5-benzodioxepine-7-carboxamido)benzoic acid, m.p. 261°–262° C.; and p-(2,3,4,5-tetrahydro-1-benzothiepine-7-carboxamido)benzoic acid, m.p. 249°–251° C.

EXAMPLE 69

The Grignard compound was prepared according to standard procedures under an argon atmosphere from 473 mg of magnesium shavings and 1.73 ml of benzyl chloride in 30 ml of tetrahydrofuran. Thereafter, 2.12 g of undiluted 3,4-dihydro- 3,3-dimethyl-2H-1,5-benzodithiepin-7-yl methyl ketone were added thereto at 0° C. and the mixture was left to react at room temperature for 1 hour. The mixture was hydrolyzed with NH$_4$Cl solution, extracted with ether, washed with water, dried and evaporated. The thus-obtained crude product was taken up in 20 ml of toluene, treated with 500 mg of p-toluenesulfonic acid and stirred at 75° C. overnight. Dehydration and isomerization took place. The solvent was removed in a vacuum and the residue was purified by column chromatography on silica gel (petroleum ether). Recrystallization from hexane finally gave 1.75 g of 3,4-dihydro-3,3-dimethyl-7-[(E)-α-methyl-styryl]-2H- 1,5-benzodithiepine as white crystals of melting point 76°–77° C.

3,4-Dihydro-3,3-dimethyl-7-[(E)-α-methylstyryl)-2H-1,5-benzodioxepine, melting point 45°–48° C., was prepared in an analogous manner.

EXAMPLE 70

The following are additional examples of compounds of formula I:
3,4-Dihydro-4,4-dimethyl-6-[(E)-α-methyl-p-[2-(tetrahydro-4'H-1,4-thiazin-4'-yl)ethoxy]styryl]-2H-1-benzothiopyran 1',1'-dioxide, m.p. 153°–154° C.;

methyl p-[(E)-2-(2-methyl-1,3-benzodithiol-5-yl)propenyl]benzoate, m.p. 72°–73° C. (hexane);

p-[(E)-2-(2-methyl-1,3-benzodithiol-5-yl)propenyl]-benzoic acid, m.p. 193°–195° C. (AcOEt);

ethyl p-(2,2-dimethyl-1,3-benzoxathiol-6-carboxamido)benzoate, m.p. 137°–138° C.;

p-(2,2-dimethyl-1,3-benzoxathiol-6-carboxamido)-benzoic acid, m.p. 284°–286° C.;

ethyl p-(2,2-dimethyl-1,3-benzodioxol-6-carboxamido)benzoate, m.p. 143°–144° C.;

2-[p-[(E)-3,4-(isopropylidenedioxy)-β-methylstyryl]-phenoxy]-N,N-dimethylethylamine. m.p. 54°–56° C.;

6-[(E)-p-(3,3-dimethylbutoxy)-α-methylstyryl]-3,4-dihydro-4,4-dimethyl-2H-1-benzothiopyran, m.p. 116°–117° C.;

p-[(E)-2-(3,4-dihydro-4,4-dimethyl-2H-1-benzothiopyran-6-yl]propenyl]phenol, m.p. 84°–85° C.;

p-[(E)-2-(3,4-dihydro-4,4-dimethyl-2H-1-benzothiopyran-6-yl]propenyl]phenol 1,1-dioxide, m.p. 182° C.;

methyl p-[(E)-2-(1,2,3,4-tetrahydro-1,2,3,4-tetramethyl-quinoxalin-6-yl)propenyl]benzoate, m.p. 90°–93° C.;

P-[(E)-2-(1,2,3,4-tetrahydro-1,2,3,4-tetramethyl-quinoxalin-6-yl)propenyl]benzoic acid, m.p. 199°–200° C.;

p-[(E)-2-(2,2-dimethyl-1,3-benzodioxol-5-yl)propenyl]benzoic acid, m.p. 185°–196° C.;

p-(2,2-dimethyl-1,3-benzodioxol-5-carboxamido)benzoic acid, m.p. 281°–283° C.;

ethyl p-[(E)-2-(3,4-dihydro-4,4-dimethyl-2H-1-benzothiopyran-6-yl)propenyl]phenyl carbonate, m.p. 113°–114° C.;

ethyl p-[(E)-2-(3,4-dihydro-4,4-dimethyl-2H-1-benzothiopyran-6-yl)propenyl]phenyl carbonate 1,1-dioxide, m.p. 130° C.; and 6-[(E)-p-methoxy-α-methylstyryl]-3,4-dihydro-4,4-dimethyl-2H-1-benzothiopyran, m.p. 99°–100° C. (methanol);

The following compounds can also be prepared, and further illustrate the compounds of formula I:
p-(1,4-benzodithiin-6-carboxamido)benzoic acid and its ethyl ester;

p-(1,2,3,4-tetrahydro-1,4-dimethyl-6-quinoxalinecarboxamido)benzoic acid and its ethyl ester;

p-(1,2,3,4-tetrahydro-1,2,3,4-tetramethyl-6-quinoxalinecarboxamido)benzoic acid and its ethyl ester;

4- (2-[p-[(E)-2-(1,2,3,4-tetrahydro-1,4,4-trimethyl-quinolin-6-yl]propenyl]phenoxy]ethyl]morpholine;

4-[2-[p-[(E)-2-(1,2,3,4-tetrahydro-1,4,4-trimethyl-quinolin-7-yl]propenyl]phenoxy]ethyl]morpholine;

4-[2-[p-[(E)-2-(3,4-dihydro-4,4-dimethyl-2H-1-benzothiopyran-7-yl]propenyl]phenoxy]ethyl]morpholine;

p-[(E)-2-(3,4-dihydro-4,4-dimethyl-2H-1-benzothiopyran-7-yl]propenyl]phenol;

1,2,3,4-tetrahydro-1,4,4-trimethyl-4'-(2-morpholinoethoxy)-6-quinolinecarboxanilide;

4-[2-[p-[(E)-2-(3,4-dihydro-4,4-dimethyl-2H-1-benzopyran-6-yl]propenyl]phenoxy]ethyl]morpholine;

p-[2-(3,4-dihydio-4,4,6-trimethyl-2H-1-benzopyran-7-yl)propenyl]benzoic acid;

p-[1,2,3,4-tetrahydro-1,4,4-trimethyl-7-quinolinyl)-carbamoyl]benzoic acid;

p-[2-(3,4-dihydro-4,4-dimethyl-6-methoxy-2H-1-benzothiopyran-7-yl)propenyl]benzoic acid; and 1-methyl-4-[2-[p-[(E)-2-(3,4-dihydro-4,4-dimethyl-2H-1-benzopyran-6-yl)propenyl]phenoxy]ethyl]piperazine.

EXAMPLE A

Hard gelatin capsules can be prepared as follows:

| Ingredients | | mg/capsule |
| --- | --- | --- |
| 1. | Spray-dried powder containing 75% of a compound of formula I | 200 |
| 2. | Sodium dioctylsulfosuccinate | 0.2 |
| 3. | Sodium carboxymethylcellulose | 4.8 |
| 4. | Microcrystalline cellulose | 86.0 |
| 5. | Talc | 8.0 |
| 6. | Magnesium stearate | 1.0 |
| | Total | 300 |

The spray-dried powder, which is based on the active ingredient, gelatin and microcrystalline cellulose, and which has an average particle size of the active ingredient of <1 mμ (measured by autocorrelation spectroscopy), is moistened with an aqueous solution of sodium carboxymethylcellulose and sodium dioctylsulfosuccinate and kneaded. The resulting mass is granulated, dried and sieved, and the granulate obtained is mixed with microcrystalline cellulose, talc and magnesium stearate. The powder is filled into size 0 capsules.

EXAMPLE B

Tablets can be prepared as follows:

| Ingredients | | mg/tablet |
| --- | --- | --- |
| 1. | A compound of formula I as a finely milled Powder | 500 |
| 2. | Powdered lactose | 100 |
| 3. | White maize starch | 60 |
| 4. | Povidone K30* | 8 |
| 5. | White maize starch | 112 |
| 6. | Talc | 16 |
| 7. | Magnesium stearate | 4 |
| | Total | 800 |

*a low viscosity grade polyvinylpyrrolidone

The finely milled active ingredient is mixed with lactose and a portion of the maize starch. The mixture is moistened with an aqueous solution of Povidone K30 and kneaded, and the resulting mass is granulated, dried and sieved. The granulate is mixed with the remaining maize starch, talc and magnesium stearate and pressed into tablets of suitable size.

EXAMPLE C

Soft gelatin capsules can be prepared as follows:

| Ingredients | | mg/capsule |
| --- | --- | --- |
| 1. | A compound of formula I | 50 |
| 2. | Triglyceride | 450 |
| | | 500 |

10 g of a compound of formula I are dissolved in 90 g of medium-chain triglyceride with stirring, inert gasification and protection from light. This solution is processed as the capsule fill mass to give soft gelatin capsules containing 50 mg of active ingredient.

EXAMPLE D

A solution can be prepared as follows:

| Ingredients | | |
| --- | --- | --- |
| 1. | A compound of formula I, finely milled | 3.0 g |
| 2. | Carbopol 934 | 0.6 g |
| 3. | Sodium hydroxide | q.s. ad pH 6 |
| 4. | 94% ethanol | 50.0 g |
| 5. | Deionized water | 100.0 g |

The active ingredient is worked into the 94% ethanol/water mixture while protecting from light. Carbopol 934 is stirred in until gelling is complete and the pH value is adjusted with sodium hydroxide.

We claim:

1. A compound of the formula

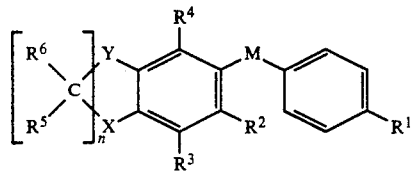

I wherein $R^1$ is hydrogen, acyl, lower-alkyl, —CHO, —CH$_2$OR$^{10}$, —COR$^7$ or OR$^{13}$; $R^2$, $R^3$ and $R^4$ are, independently hydrogen, lower-alkyl, lower-alkoxy or halogen; $R^5$ and $R^6$ are, independently, hydrogen or lower-alkyl; $R^7$ is hydroxy, lower-alkoxy or NR$^8$R$^9$; $R^8$ and $R^9$ are, independently, hydrogen or lower-alkyl; one of X and Y is >CR$^{14}$R$^{15}$, and the other is —O—; $R^{10}$ is hydrogen, lower-alkyl or acyl; M is —C(R$^{11}$)=C(R$^{12}$)—, —CONH— or —NH—CO—; $R^{11}$, $R^{12}$, $R^{14}$ and $R^{15}$ are, independently, hydrogen or lower-alkyl, $R^{13}$ is hydrogen, lower-alkoxycarbonyl or lower-alkyl, which can be substituted by amino, mono-alkylamino, di-alkylamino, morpholino, thiomorpholino or piperazino, and n is 1, 2, 3 or 4 provided that $R^1$ is OR$^{13}$ when M is —C(R$^{11}$)=C(R$^{12}$)— and $R^1$ is hydrogen, acyl, lower-alkyl, —CH$_2$OR$^{10}$, or OR$^{13}$ when M is —CONH— or a salt of a compound of formula I, when $R^1$ is carboxy.

2. A compound in accordance with claim 1, wherein $R^{13}$ is hydrogen or unsubstituted lower-alkyl or lower-alkyl substituted by amino, mono-alkylamino, di-alkylamino, morpholino, thiomorpholino or piperazino.

3. A compound in accordance with claim 2, wherein M is —C(R$^{11}$)=C(R$^{12}$)—.

4. A compound in accordance with claim 2, wherein M is —CONH—.

5. A compound in accordance with claim 3, wherein Y is —O—.

6. A compound in accordance with claim 4, wherein Y is —O—.

7. A compound of claim 1, wherein the compound is 3,4,-dihydro-4,4-dimethyl-7-(α-methylstyryl)-2H-1-benzopyran.

8. A compound of claim 1, wherein the compound is 4-[2-[p-[(E)-2-(3,4-dihydro-4,4-dimethyl-2H-1-benzopyran-6-yl]propenyl]phenoxy]ethyl]morpholine.

9. A pharmaceutical composition comprising a compound of the formula

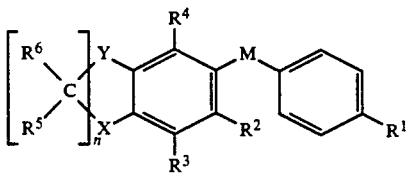

wherein $R^1$ is hydrogen, acyl, lower-alkyl, —CHO, —CH$_2$OR$^{10}$, —COR$^7$ or OR$^{13}$; $R^2$, $R^3$ and $R^4$ are, independently, hydrogen, lower-alkyl, lower-alkoxy or halogen; $R^5$ and $R^6$ are, independently, hydrogen or lower-alkyl; $R^7$ is hydroxy, lower-alkoxy or NR$^8$R$^9$; $R^8$ and $R^9$ are, independently, hydrogen or lower-alkyl; one of X and Y is >CR$^{14}$R$^{15}$, and the other is —O—; $R^{10}$, is hydrogen, lower-alkyl or acyl; M is —C(R$^{11}$)=C(R$^{12}$)—, —CONH— or —NH—CO—; $R^{11}$, $R^{12}$, $R^{14}$ and $R^{15}$ are, independently, hydrogen or lower-alkyl, $R^{13}$ is hydrogen, lower-alkoxycarbonyl or lower-alkyl, which can be substituted by amino, monoalkylamino, di-alkylamino, morpholino, thiomorpholino or piperazino, and n is 1, 2, 3 or 4 provided that $R^1$ is OR$^{13}$ when M is —C(R$^{11}$)=C(R$^{12}$)— and $R^1$ is hydrogen, acyl, lower-alkyl, —CH$_2$OR$^{10}$, or OR$^{13}$ when M is —CONH— or a salt of a compound of formula I, when $R^1$ is carboxy and an inert carrier.

10. A pharmaceutical composition in accordance with claim 9, wherein $R^{13}$ is hydrogen or unsubstituted lower-alkyl or lower-alkyl substituted by amino, monoalkylamino, di-alkylamino, morpholino, thiomorpholino or piperazino.

11. A pharmaceutical composition in accordance with claim 10, wherein M is —C(R$^{11}$)=C(R$^{12}$)—.

12. A pharmaceutical composition in accordance with claim 10, wherein M is —CONH—.

13. A pharmaceutical composition in accordance with claim 11, wherein Y is —O—.

14. A pharmaceutical composition in accordance with claim 12, wherein Y is —O—.

15. A method of treating inflammatory, allergic, rheumatic and immunological disorders which comprises administering to a host requiring such treatment an effective amount of a compound of the formula

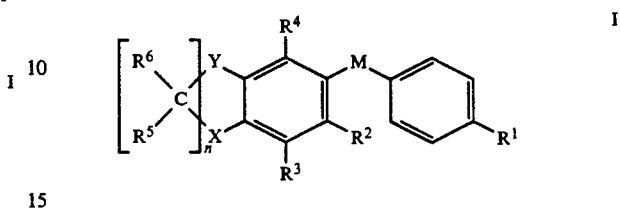

wherein $R^1$ is hydrogen, acyl, lower-alkyl, —CHO, —CH$_2$OR$^{10}$, —COR$^7$ or OR$^{13}$; $R^2$, $R^3$ and $R^4$ are, independently, hydrogen, lower-alkyl, lower-alkoxy or halogen; $R^5$ and $R^6$ are, independently, hydrogen or lower-alkyl; $R^7$ is hydroxy, lower-alkoxy or NR$^8$R$^9$; $R^8$ and $R^9$ are, independently, hydrogen or lower-alkyl; one of X and Y is >CR$^{14}$R$^{15}$, and the other is —O— $R^{10}$ is hydrogen, lower-alkyl or acyl; M is —C(R$^{11}$)=C(R$^{12}$)—, —CONH— or —NH—CO—; $R^{11}$, $R^{12}$, $R^{14}$ and $R^{15}$ are, independently, hydrogen or lower-alkyl, $R^{13}$ is hydrogen, lower-alkoxycarbonyl or lower-alkyl, which can be substituted by amino, monoalkylamino, di-alkylamino, morpholino, thiomorpholino or piperazino, and n is 1, 2, 3 or 4 provided that $R^1$ is OR$^{13}$ when M is —C(R$^{11}$)=C(R$^{12}$)— and $R^1$ is hydrogen, acyl, lower-alkyl, —CH$_2$OR$^{10}$, or OR$^{13}$ when M is —CONH— or a salt of a compound of formula I, when $R^1$ is carboxy.

16. A method composition in accordance with claim 15, wherein $R^{13}$ is hydrogen or unsubstituted lower-alkyl or lower-alkyl substituted by amino, monoalkylamino, di-alkylamino, morpholino, thiomorpholino or piperazino.

17. A method in accordance with claim 16, wherein M is —C(R$^{11}$)=C(R$^{12}$)—.

18. A method in accordance with claim 16, wherein M is —CONH—.

19. A method in accordance with claim 17, wherein Y is —O—.

20. A method composition in accordance with claim 18, wherein Y is —O—.

* * * * *

UNITED STATES PATENT AND TRADEMARK OFFICE
CERTIFICATE OF CORRECTION

PATENT NO. : 5,300,522

DATED : April 5, 1994

INVENTOR(S) : Michael Klaus, Peter Mohr, Ekkehard Weiss

It is certified that error appears in the above-identified patent and that said Letters Patent is hereby corrected as shown below:

-Claim 1, Column 34, Lines 41-42: "independently" should read
--- independently, --- .

-Claim 15, Column 36, Line 22: " -O- " should read
--- -O-; --- .

Signed and Sealed this

Eighteenth Day of April, 1995

BRUCE LEHMAN

*Attest:*

*Attesting Officer*

*Commissioner of Patents and Trademarks*